US010571371B2

(12) United States Patent
Marini et al.

(10) Patent No.: US 10,571,371 B2
(45) Date of Patent: Feb. 25, 2020

(54) COMPOSITIONS AND METHODS FOR CLEARING A BIOLOGICAL SAMPLE

(71) Applicant: WAKE FOREST UNIVERSITY HEALTH SCIENCES, Winston-Salem, NC (US)

(72) Inventors: Frank Marini, Winston-Salem, NC (US); George Christ, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 381 days.

(21) Appl. No.: 15/502,081

(22) PCT Filed: Aug. 7, 2015

(86) PCT No.: PCT/US2015/044376
§ 371 (c)(1),
(2) Date: Feb. 6, 2017

(87) PCT Pub. No.: WO2016/023009
PCT Pub. Date: Feb. 11, 2016

(65) Prior Publication Data
US 2017/0227430 A1  Aug. 10, 2017

Related U.S. Application Data

(60) Provisional application No. 61/999,885, filed on Aug. 7, 2014.

(51) Int. Cl.
*G01N 1/30* (2006.01)
*G01N 1/36* (2006.01)
*G01N 1/40* (2006.01)
*G01N 33/483* (2006.01)
*G06T 7/00* (2017.01)

(52) U.S. Cl.
CPC ............... *G01N 1/30* (2013.01); *G01N 1/36* (2013.01); *G01N 1/4044* (2013.01); *G01N 33/4833* (2013.01); *G01N 2001/364* (2013.01); *G06T 7/0012* (2013.01)

(58) Field of Classification Search
None
See application file for complete search history.

(56) References Cited

U.S. PATENT DOCUMENTS

| 5,151,502 | A | * | 9/1992 | Webb | .................. | C07K 14/72 |
| | | | | | | 435/70.1 |
| 2004/0259162 | A1 | | 12/2004 | Kappel et al. | | |
| 2006/0046261 | A1 | | 3/2006 | Porter et al. | | |
| 2007/0172911 | A1 | | 7/2007 | Farrell et al. | | |
| 2013/0045503 | A1 | * | 2/2013 | Miyawaki | ................ | G01N 1/30 |
| | | | | | | 435/40.5 |

FOREIGN PATENT DOCUMENTS

WO   WO-2014/025392 A1   2/2014

OTHER PUBLICATIONS

Burmeister et al., "Age-Related Alterations in Regeneration of the Urinary Bladder after Subtotal Cystectomy," Am J Path 183(5):1585-95 (2013).
Burmeister et al., "Early Stages of in Situ Bladder Regeneration in a Rodent Model," Tissue Engineering 16:2541-2551 (2010).
Calle et al. "The use of optical clearing and multiphoton microscopy for investigation of three-dimensional tissue-engineered constructs," Tissue Engineering, 8 pages (2014).
Chung et al. "Clarity for mapping the nervous system," Nature Methods 10(6):508-513 (2013).
Chung et al., "Structural and molecular interrogation of intact biological systems," Nature, 8 pages (2013).
Corona et al., "Implantation of in Vitro Tissue Engineered Muscle Repair Constructs and Bladder Acellular Matrices Partially Restore In Vivo Skeletal Muscle Function in a Rat Model of Volumetric Muscle Loss Injury," Tissue Eng. Part A 20:705-715 (2014).
Dickie et al., "Three-dimensional visualization of microvessel architecture of whole-mount tissue by confocal microscopy," Microvascular Research 72:20-26 (2006).
Fu et al., "Microtome-Free 3-Dimensional Confocal Imaging Method for Visualization of Mouse Intestine with Subcellular-Level Resolution," Imaging and Advanced Technology, AGA Institute 453-465 (2009).
Gonzalez-Billido et al. "Labeling and Confocal Imaging of Neurons in Thick Inverterbrate Tissue Samples," Cold Spring Harb Protoc (2012).
Hama et al., "Scale: a chemical approach for fluorescence imaging and reconstruction of transparent mouse brain," Nature Neuroscience 14(11):1481-1490 (2011).
Hirshburg et al., "Correlation Between Collagen Solubility and Skin Optical Clearing Using Sugars," Lasers Surg. Med. 39(2):140-144 (2007).
International search report and written opinion from PCT/US15/44376 dated Nov. 9, 2015.
Ke et al., "SeeDB: a simple and morphology-preserving optical clearing agent for neuronal circuit reconstruction," Nat. Neurosci. 16(8):1154-61 (2013).
Levene et al., "Multiphoton microscopy of cleared mouse organs," J. Biomed Opt. 15(3):036017 (2010).

(Continued)

*Primary Examiner* — Christine Foster
*Assistant Examiner* — Ellen J Marcsisin
(74) *Attorney, Agent, or Firm* — Marshall, Gerstein & Borun LLP

(57) ABSTRACT

The disclosure provides improved materials and methods for optically clearing biological tissue that is subsequently used for deep tissue imaging analysis. Also provided is a description of a microscopic image acquisition methodology in which imagery of intact tissues are acquired to rapidly acquire microscopy data on a whole-organ scale to maximize cost effectiveness for biological microscopy and minimize time spent performing such analysis.

28 Claims, 17 Drawing Sheets

(56) References Cited

OTHER PUBLICATIONS

Liu et al., "3-D illustration of network orientations of interstital cells of Cajal subgroups in human colon as revealed by deep-tissue imaging with optical clearing," Am J Physiol Gastrointest Liver Physiol. 302(10):G1099-G1110 (2012).

Machingal et al., "A Tissue-Engineered Muscle Repair Construct for Functional Restoration of an Irrecoverable Muscle Injury in a Murine Model," Tissue Eng Part A 17:2291-2303 (2011).

Peyton et al., "Characterization of the Early Proliferative Response of the Rodent Bladder to Subtotal Cystectomy: A Unique Model of Mammalian Organ Regeneration," PLoS One 7(10):e47414 (2012).

Renier et al., "iDISCO: A Simple, Rapid Method to Immunolabel Large Tissue Samples for Volume Imaging," Cell, 159:1-15 (2014).

Selever et al., "A Rapid Approach to High-Resolution Fluorescence Imaging in Semi-Thick Brain Slices," J. Vis. Exp. 26(53):1-5 (2011).

Smith et al., "Nondestructive Optical Determination of Fiber Organization in Intact Myocardial Wall," Microscopy Research and Technique 71:510-516 (2008).

Staudt et al., "2,2'-Thiodiethanol: A New Water Soluble Mounting Medium for High Resolution Optical Microscopy," Microsc. Res. Tech. 70:1-9 (2007).

Susaki et al., "Whole-Brain Imaging with Single-Cell Resolution Using Chemical Cocktails and Computational Analysis," Cell, 157:726-739 (2014).

Sun et al., "Nonlinear optical microscopy: use of second harmonic generation and two-photon microscopy for automated quantitative liver fibrosis studies," J. Biomed. Opt. 13(6:064010 (2008).

Tainaka et al., "Whole-Body Imaging with Single-Cell Resolution by Tissue Decolorization," Cell, 159:911-924 (2014).

Tomer et al., "Advanced Clarity for rapid and high-resolution imaging of intect tissues," Nature Protocols, 9(7):1682-1697 (2014).

Yang et al., "Single-Cell Phenotyping within Transparent Intact Tissue Through Whole-Body Clearing," Cell 158:1-14 (2014).

* cited by examiner

400 μm

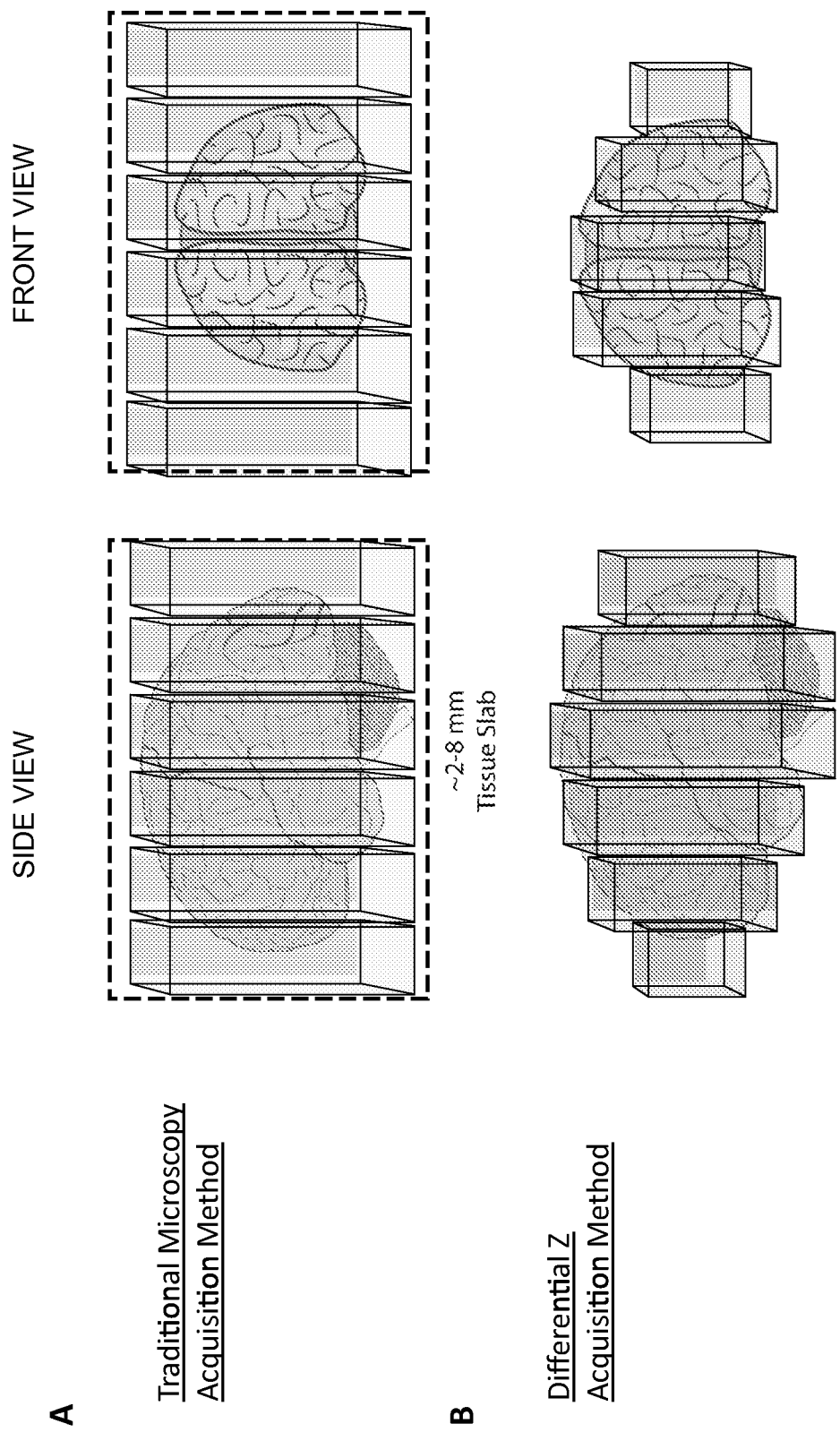

COMPOSITIONS AND METHODS FOR CLEARING A BIOLOGICAL SAMPLE

CROSS REFERENCE TO RELATED APPLICATIONS

This application claims the priority benefit under 35 U.S.C. § 119(e) of Provisional U.S. Patent Application No. 61/999,885, filed Aug. 7, 2014, the disclosure of which is incorporated herein by reference in its entirety.

STATEMENT OF GOVERNMENT INTEREST

This invention was made with government support under grant numbers NIDDK-1P20 DK097806-01, NCI-P50 CA083639, and NCI-1R01 NS069964 awarded by the National Institutes of Health. The government has certain rights in the invention.

FIELD OF THE INVENTION

The present disclosure relates to compositions and methods that are useful in optically clearing a biological sample so as to make the sample transparent.

BACKGROUND OF THE INVENTION

As imaging technology improves via advances including better optics, higher resolutions, and the ability to image deeper into tissue with three dimensional results, there is a higher demand for more advanced imaging protocols to image tissue on a large scale.

One of the biggest issues with imaging the entirety of an organ, or even a relatively small sample of tissue (e.g., 1 mm×1 mm), is the difficulty of using traditional immunohistochemical (IHC) techniques to achieve the large scale results that are desirable. Typical IHC procedures require the embedding of the sample into paraffin or snap frozen into an optimum cutting temperature (OCT)-based block. Paraffin is useful for subsequent antibody labeling but will remove any endogenous fluorescence localized in the tissue. The frozen blocks will retain a certain amount of fluorescence, however they will damage or destroy a lot of microstructures in the tissue. Once embedded with one of the above methods, the blocks then have to be sliced into extremely thin, approximately 4 micrometers (μm), slices that are processed and put onto slides for staining and imaging. With 4 μm slices, it would take 250 separate slices for a 1 millimeter (mm) thick tissue, which would have to be put onto slides for subsequent staining and imaging. This procedure would therefore take an unacceptable amount of time for the tissue preparation alone. Time is not the only concern with these methods, however. By cutting the tissue, damage to the edges of each tissue slice is inevitable. This damage will create "gaps" and damaged areas in between each tissue slice when all of the slices are aligned and reconstructed. Furthermore, the actual imaging of these 250 tissue slices would take an unacceptable amount of time. Most oil-dipping objectives don't even have a working distance long enough to image through the entirety of a 4 μm thick tissue slice. Even if all of the slices are fully imaged through the entirety of the slice thickness, the ability to align and accurately reconstruct the sample would be extremely difficult.

Due to the aforementioned difficulties that arise when performing tissue analysis on a larger (macro) scale, researchers have turned to using multiphoton imaging with a whole mounted, unsectioned specimen for deep tissue imaging. This technique allows one to use a planar focused laser to optically slice through the tissue, obviating the need for sectioning. Such a technique, however, carries with it a vast number of limitations and problems that arise when performing deep tissue imaging. One of the most notable issues is the inability to limitlessly image into the depth of the tissue. Under the most optimal conditions, imaging of tissue up to 1000 μm in very low autofluorescent tissue has been achieved [Levene, et al. J. Biomed Opt, 2010, 15(3): 036017]. However, attaining such a result is extremely difficult and rare with all tissues, most notably the brain. Realistically, most deep tissue imaging can currently be performed up to a range of about 300-500 μm.

The inability to image deeper into the tissue arises from light absorption, and light scattering caused by lipids in the tissue. Not only do the lipids create an extreme autofluorescent signal, specifically in adipose or in tissues with high lipid content, such as liver, but they also create light scattering of the fluorescent signal and the input laser signal. There have been many attempts at combating the light scattering issue that arises from lipids [Nonlinear optical microscopy: use of second harmonic generation and two-photon microscopy for automated quantitative liver fibrosis studies. Sun W, Chang S, Tai D C, Tan N, Xiao G, Tang H, Yu H., J Biomed Opt. 2008 November-December; 13(6): 064010].

One of the more basic attempts at clearing tissue has been through the use of sucrose solutions to clear the tissue [SeeDB: a simple and morphology-preserving optical clearing agent for neuronal circuit reconstruction. Ke M T, Fujimoto S, Imai T. Nat Neurosci. 2013 August; 16(8):1154-61. Correlation between collagen solubility and skin optical clearing using sugars. Hirshburg J, Choi B, Nelson J S, Yeh A T. Lasers Surg Med. 2007 February; 39(2):140-4]. While there has been some success with very small pieces of tissue, large samples cannot be used. There are multiple concerns involved with this clearing technique. Sucrose causes a dehydration of the tissue, ultimately causing shrinkage of the actual tissue, most likely due to extreme osmolality changes. The shrinkage of the tissue does not provide accurate information about the structure of the tissue, specifically the microstructure. This technique does not permit the ability to label the tissue with antibodies. Also, the sucrose solutions do not provide a good medium for maintaining endogenous fluorescence. The light transmittance with sucrose-cleared tissues is also extremely poor. True and complete clearing using sucrose clearing is unattainable.

Glycerol clearing has also been performed on smaller sample sizes [A rapid approach to high-resolution fluorescence imaging in semi-thick brain slices. Selever J, Kong J Q, Arenkiel B R., J Vis Exp. 2011 Jul. 26; (53)]. The limitations of this technique are very similar to those mentioned in the sucrose technique. Glycerol can only be used on extremely small and thin samples. There is a smaller volume change in the sample when using glycerol; however, volume change does still occur. Antibody labeling cannot be utilized with this technique. Glycerol is also a very poor medium for endogenous fluorescence since it has been shown to quench a majority of the fluorescence. The light transmittance with glycerol is actually much better than sucrose when using a proper objective that matches the glycerol refractive index (RI) in the tissue. True complete clearing using glycerol clearing is typically unachievable.

Another technique that has shown relative success in clearing tissue is called benzyl alcohol and benzyl benzoate (BABB). The technique also uses tetrahydrofuran (THF) to aid in the clearing process. While this technique does in fact actually "clear" the tissue, there are many concerns. BABB causes the most drastic tissue shrinkage out of all the clearing techniques demonstrated in literature, thus creating the worst tissue structure representation. BABB also entirely quenches the endogenous fluorescence of the sample. The THF and BABB solutions are also highly caustic to use, thus extreme care must be utilized to perform this technique. The light transmittance through BABB cleared tissue is still rather poor although better than sucrose or glycerol. Antibody labeling is also unachievable with this technique.

A more recent technique that introduced an era that is expanding our abilities for deep tissue imaging is called SCALE [Hama et al., Nature Neuroscience 14(11): 1481-1490 (2011)]. SCALE is a clearing reagent containing a concentrated urea solution in which the sample incubates until the tissue is cleared. Such incubation can require weeks to months with regular media exchanges. One mechanism by which this may occur is through the superhydrating effects that the solution has on the tissue. The SCALE technique has allowed researches to image up to 8 mm through brain tissue with a resolution better than what is achieved when deep tissue imaging in a normal whole mount tissue. Fluorescence is adequately maintained and the technique is easy to perform. However, the major limitations are (i) the inability to do antibody labeling, (ii) the approximate 1.5× volume expansion of the tissue, and (iii) the amount of time that it takes to perform the technique. Clearing a whole mouse brain can take anywhere from 4 weeks to 6 months. This technique also led to the creation of a SCALE-specific objective series from Olympus that consists of 4 mm and 8 mm working distance objectives that are specifically refractive index matched to the SCALE solution. While this technique has provided some advantages in the field of tissue clearing, it also possesses limitations. For example, SCALE results in a denaturation of the majority of proteins from the sample, there is an inability to probe with antibodies in the SCALE solution, and the majority of fluorescent signal is lost in a time dependent manner.

A recent clearing technique that has been demonstrated is SeeDB. This technique has been shown to be successful at clearing tissue with a technically simple method. SeeDB utilizes gradient washes of the tissue in Fructose/1-Thioglycerol solutions for rather short periods of time, approximately 12 hours. This creates a cleared specimen in about 7 days. SeeDB is also able to retain fluorescent signal in the tissue. SeeDB also provides the best light transmittance compared to earlier techniques, as well as a lack of shrinking or expansion of the actual tissue. SeeDB does not, however, allow antibody staining and the cleared sample can only be maintained in the final clearing solution for a maximum of 7 days, at which time the sample has to be washed free of fructose. There have also been a lot of problems reported with autofluorescence and browning developing in the tissue due to a maillard reaction. This technique has also not been proven to completely clear the entirety of an organ; in fact, the technique performs best with tissue slices that are about 1-2 millimeters in thickness. One of the main benefits of this technique is the high refractive index that is achieved with the final sample, 1.51. This matches most oil immersion objectives and allows for an incredibly high optical resolution. A custom high refractive index objective has also been created by Olympus to accommodate this higher RI.

Probably the most notable of clearing techniques to recently be published is called CLARITY. CLARITY takes a completely different approach to clearing the tissue than those mentioned above. CLARITY actually delipidates the tissue, thus removing the cause of the light scattering: lipids. In order to achieve such delipidation with minimal loss of proteins, the sample is embedded into an acrylamide-based gel that is polymerized into the sample. This causes a crosslinking effect that binds the proteins and such, without binding to the actual lipids. Such crosslinking allows for removal of the lipids with limited damage to the rest of the components of the tissue. It has been shown that the microstructures of the tissues are kept intact. CLARITY utilizes an Electrophoresis Tissue Clearing Chamber (ETC), with an SDS-based buffer, that accelerates the removal of the lipids from the sample. The cleared tissue is then washed and the refractive index matched in either FocusClear™ or 80% glycerol for imaging. The major benefit of CLARITY is that antibody penetration is possible due to the complete removal of the lipids from the sample. It has been demonstrated that antibodies can be probed, imaged, and stripped for subsequent antibody labeling experiments. The ability to keep the tissue structurally accurate is also another benefit. The problems with CLARITY arise with the variety of tissues that are compatible with the technique. CLARITY was developed primarily to focus on clearing the mouse brain for brain mapping experiments. While it has been shown that this works for nervous tissue, it is not as compatible with other organs/tissues in the body. Attempts at using the CLARITY technique on other parts of the mouse were met with very little success. (See, e.g., the CLARITY Resources website.) Other tissues burn, form black on the outside, turn brown/yellow, and even degrade. Researchers have also reported difficulty even when attempting to clear the brain (see, e.g., the CLARITY Resources website). The protocol itself is technically difficult to perform, while also being tremendously costly. There is also an inability to perform the clearing technique on multiple samples if only one chamber is created. It is therefore an ineffective technique if one is attempting a round of experiments that would require clearing of a dozen or more samples. Another confounding factor is the mounting medium. FocusClear™ has been shown to be a great product for tissue clearing; however, it is prohibitively costly. FocusClear™ has also been demonstrated to reduce fluorescent signals, quenching signals such as green/red fluorescent protein (GFP/RFP). (See, e.g., the CLARITY Resources website). An alternative to FocusClear™ is glycerol, which, as stated above, is not very compatible with fluorescence. Researchers in general have also been reporting a significant loss of endogenous GFP fluorescence when performing CLARITY. (See, e.g., the CLARITY Resources website.)

SUMMARY OF THE INVENTION

The present disclosure is therefore directed to providing improved reagents, compositions, and methods for uniquely clearing lipids from a biological sample.

Accordingly, in one aspect, the disclosure provides a method for removing lipid from a biological sample, the method comprising: contacting a fixed biological sample with a composition in an amount and for a time sufficient to remove lipid, the composition comprising sodium dodecyl sulfate (SDS), 3-(N,N-Dimethylmyristylammonio)propanesulfonate (SB3-14), Tween® 20, Triton™ X-100, sodium deoxycholate, and a salt; wherein the contacting results in the sample being significantly free of lipid. In some embodiments, contacting comprises perfusing the biological sample with the composition.

In some embodiments, the composition comprises about 1% to about 10% (weight:volume) of SDS. In some embodiments, the composition comprises about 0.03% to about 3% (weight:volume) SB3-14.

In further embodiments, the composition comprises about 0.3% to about 3% (weight:volume) Tween® 20, while in still further embodiments, the composition comprises about 0.3% to about 3% (weight:volume) Triton™ X-100. In some embodiments the composition comprises about 0.1% to about 1% (weight:volume) sodium deoxycholate.

The disclosure also provides embodiments wherein the composition has a pH of from about 7 to about 9. In further embodiments, the composition has a pH of from about 7.8 to about 8.8, and in still further embodiments the composition has a pH of from about 8.3 to about 8.5.

In some embodiments, the salt is selected from the group consisting of sodium chloride, calcium chloride, and sodium metaborate. In further embodiments, the salt is present in the composition at a concentration of from about 50 mM to about 500 mM. In still further embodiments, the salt is present in the composition at a concentration of 150 mM.

In certain embodiments, the composition does not comprise boric acid. In further embodiments, the composition does not comprise urea. In still further embodiments, the composition does not comprise Tween® 20. Thus, in some embodiments, the composition comprises sodium dodecyl sulfate (SDS), 3-(N,N-Dimethylmyristylammonio)propanesulfonate (SB3-14), Triton™ X-100, sodium deoxycholate, and a salt.

The disclosure also provides embodiments wherein the biological sample is fixed by embedding the biological sample in a fixative comprising acrylamide, paraformaldehyde, and optionally saponin.

In further embodiments, the biological sample is contacted with an antibody.

In various embodiments, methods of the disclosure further comprise contacting the biological sample with phospholipase A2 (PLA2).

Methods of the disclosure, in some embodiments, further comprise the step of contacting the biological sample with an imaging solution (i.e., a refractive index matching solution) comprising 2,2'-thiodiethanol (TDE) [Staudt et al., Microsc. Res. Tech. 70: 1-9 (2007)]. In further embodiments, the imaging solution comprises from about 1% to about 90% TDE.

In any of the embodiments disclosed herein, it is contemplated that the biological sample is obtained from a plant or a eukaryote. In some embodiments, the biological sample is obtained from a eukaryote. In further embodiments, the biological sample is an organ, a tissue, or a cell taken from a multicellular organism. In still further embodiments, the eukaryote is a mouse embryo or a zebrafish.

The disclosure also contemplates embodiments in which the organ is selected from the group consisting of heart, blood vessels, salivary gland, esophagus, stomach, liver, gallbladder, pancreas, intestine, colon, rectum, anus, endocrine gland, adrenal gland, kidney, ureter, bladder, lymph node, tonsils, adenoid, thymus, spleen, skin, muscle, brain, spinal cord, nerve, ovary, fallopian tube, uterus, vagina, mammary gland, testes, prostate, penis, pharynx, larynx, trachea, bronchi, lung, diaphragm, cartilage, ligaments, and tendon.

An advantage provided by the present disclosure is the ability to image a biological tissue on a macroscale and at a resolution that has not previously been achieved. Accordingly, in some embodiments, methods of the disclosure further comprise imaging the biological sample.

In some embodiments, that imaging is macroscale imaging. In further embodiments, the macroscale imaging results in the ability to visualize the sample to a depth of about 5 µm. In still further embodiments, the macroscale imaging results in the ability to visualize the sample to a depth of about 100 µm. In some embodiments, the macroscale imaging results in the ability to visualize the sample to a depth of about 200 µm. In some embodiments, the macroscale imaging results in the ability to visualize the sample to a depth of about 500 µm. In still further embodiments, the macroscale imaging results in the ability to visualize the sample to a depth of about 1 mm, and in further embodiments the macroscale imaging results in the ability to visualize the sample to a depth of about 10 mm. In yet additional embodiments, the macroscale imaging results in the ability to visualize the sample to a depth of about 11 mm, or about 12 mm, or about 13 mm, or about 14 mm, or about 15 mm, or about 16 mm, or about 17 mm, or about 18 mm, or about 19 mm, or about 20 mm.

In any of the embodiments of the disclosure, the imaging provides three-dimensional information.

In another aspect, the disclosure provides a package or a kit comprising (i) a composition as disclosed herein in one or more containers, and (ii) instructions for use.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows is an image of approximately 3 mm thick tissue section of the middle portion of the mouse bladder (i.e., dome (top) and base (bottom) of bladder are not shown). This bladder was obtained from a collagen 1 expressing mouse, and the green color (labeled as "urothelium") reflects cellular material, while the red color (labeled as "bladder wall") reflects the 2nd harmonic generated by the imaging of the extracellular matrix surrounding the bladder tissue. FIGS. 1B and 1C illustrate an enlarged version of region shown in box in panel 1A. FIG. 1B) Cells native to bladder tissue; FIG. 1C) Collagen/ECM components. Scale bar=100 µm.

FIG. 3A) Collagen/Fibrillar ECM Structures; FIG. 3B) Cells/parenchyma. ROI denotes area of regeneration. Scale bars=150 µm.

FIG. 8F shows a computer-aided-design (CAD) schematic of the chamber optimized for rapidly perfusing the lipid magnet through tissues. At left, tissues are loaded into histology cartridges for processing. A total of either 9 large or 18 small cartridges, or any combination, fit into the nine slots of the chamber. Top right, front view. Bottom right, default view highlighting the inlet to the chamber as well as the supporting structures used to mount screw threads.

FIG. 10 depicts an image acquisition method referred to herein as "Differential Z scanning" which maximizes data collection while minimizing acquisition time required for performing whole-organ imaging using the optical tissue clearing technology described herein.

DETAILED DESCRIPTION OF THE INVENTION

Figure 1A:
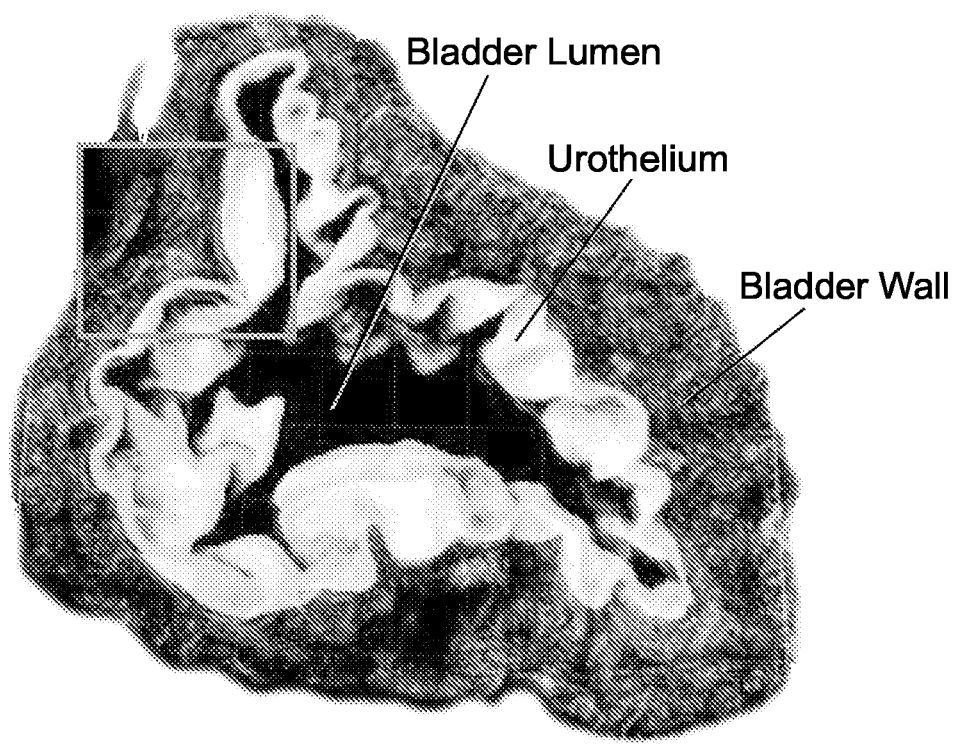
FIGS. 1A-1C depict macro scale imaging with cellular level resolution of normal rat bladder.

In general, the disclosure provides improved methods of removing lipids from a biological sample. According to the methods described herein, after a biological sample of interest has been embedded, lipids are removed using a high-pressure perfusion system.

The requirements for an optimal clearing technique to remove lipids from a biological sample include little or no expansion or swelling of the biological sample, the ability to probe the biological sample with antibodies, minimal amount of protein loss from the biological sample, high throughput biological sample clearing, the ability to match the refractive index (RI) of the biological sample to the RI of microscope objectives, cost-efficiency, short time periods for clearing the biological sample, the ability to clear any biological sample of interest, and minimal technical details. There are currently no techniques that address all of the aforementioned requirements. Thus, the present disclosure provides a formulation for a buffer, the "lipid magnet," which allows one to achieve rapid clearing of a biological sample of interest for high quality deep tissue imaging analysis. The present disclosure also provides, inter alia, enhanced refractive index matching ability, as well as image acquisition procedures that maximize data collection while minimizing acquisition time required for performing whole-organ imaging.

The lipid magnet formulation was created based on a detergent system that is intended to create a mixed micelle population that will strip the lipids away from the tissue, utilizing the mechanical stress provided by the high-pressure perfusion of the buffer. Sodium dodecyl sulfate (SDS) and sodium deoxycholate are both used in conjunction to provide anionic detergents. These anionic detergents are often found in lysis buffers together to improve the solubilization of membranes. Triton X-100 and Tween-20 are used in conjunction to provide non-ionic detergents. These nonionic detergents are often found in wash buffers. SB3-14 is provided as an affordable but effective zwitterionic detergent. The NaCl is added to keep the ionic strength of the buffer at a human physiological salt concentration. All of these detergent concentrations are at least 4-fold higher than the critical micelle concentration (CMC), thus effective micelle formations occur and the detergents will not precipitate out.

A "biological sample" as used herein generally refers to any material derived from a plant or an animal. When derived from an animal, the animal can be any animal including fish, amphibians, reptiles, birds, and mammals. The mammal is selected from the group consisting of a laboratory, farm or domesticated animal including without limitation a mouse, a rat, a rabbit, a guinea pig, a primate, a dog, a cat, a cow, and a horse. Mammals also include a human. "Material" includes an organ (a collection of tissues joined in a structural unit to serve a common function) and a tissue (plant or animal). In some embodiments, the biological sample is the entire organism. For example and without limitation, the biological sample can in some embodiments be a nematode, a fruit fly, or a zebrafish.

As used herein, "delipidate" is understood to mean the process by which lipids are removed from a biological sample using a method disclosed herein. In various embodiments, the lipid content of the delipidated biological sample is decreased relative to the biological sample prior to being subjected to a method of the disclosure. The decrease in lipid content in the delipidated biological sample is, in various embodiments, about 10%, about 20%, about 30%, about 40%, about 50%, about 60%, about 70%, about 80%, about 90% or more compared to the biological sample prior to being subjected to a method of the disclosure.

As described above, the compositions and methods of the disclosure provide several advantages over optical clearing techniques known in the art. First, the methods disclosed herein are highly versatile.

The second advantage relates to the high throughput ability of the methods disclosed herein versus techniques known in the art. The CLARITY technique uses a "CLARITY chamber method" which accommodates only one tissue at a time. Methods disclosed herein allow for the perfusion of 30 tissues in one chamber.

Third, the methods of the disclosure allow one to stain a sample with an antibody whereas other known techniques (e.g., SCALE and SeeDB) do not. Fourth, a significant drawback of other methods known in the art is the loss of fluorescent signal in a sample. Focusclear™, the product chosen for refractive index matching with other techniques, is known for this. Using the methods of the disclosure, however, the issue of fluorescence loss is avoided.

Fifth, the output of data generated using the methods of the disclosure can be used for structure/function assessment as a macroscopic three dimensional topographical reconstruction. Using the methods of the disclosure allows for an advanced capacity to understand what cells and extracellular matrix (ECM) are doing in a given sample (e.g., the brain). Such three dimensional imaging permits determination and/or elucidation of structure-function relationships within and between tissues. For example and without limitation, the methods of the disclosure for clearing lipids from a biological sample enable 3D topographical reconstructions, single cell resolution, structure-function relationships and 3D contextual relationships of intact tissue (e.g., stressor and tension assessments of fibrils and proteins in relation to a matrix; quantitate how a particular tissue relates to and interacts with another tissue; quantitate mechanical forces and effects), pathological differences between samples, quantify tissue organization and tissue disorganization, and contrast structure and function of regenerative versus native organs and tissues. As another non-limiting example of the utility of the methods disclosed herein, and of particular interest in the field of regenerative medicine, is the ability to induce stem cell populations to produce ECM when treating traumatic volumetric muscle loss injuries (VML). Functional recovery of VML injuries using bioengineered tissues is dependent on promoting stem cells to produce matrix in an organized manner. In some preclinical applications, it has been demonstrated [see, e.g., Corona et al., Tissue Eng Part A 20: 705-715 (2014); and Machingal et al., Tissue Eng Part A 17: 2291-2303 (2011)] that different biomaterial scaffolds used in tissue engineering for murine VML injuries demonstrate varying degrees of functional recovery in vivo. Given that stem cell-deposited ECM serves as a structural signal for directing the growth of regenerating myofibrils—the key component for muscle generation—the structural organization of ECM has a direct correlation on assessing the cellular mechanisms that direct specific functional outcomes in regenerating tissue.

Finally, the methods of the disclosure provide enhanced refractive index matching relative to methods described in the art. For example, the SCALE, SeeDB, and CLARITY methods require a custom microscope objective with a refractive index collar to match somewhere between 1.38-1.48 numerical aperture (NA). Using methods disclosed herein, the objective one chooses is irrelevant. The present disclosure allows one to index match to all objectives heretofore tested.

The disclosure thus provides improved methods of optically clearing any biological tissue of interest using a solution that is termed a "lipid magnet" for its ability to delipidate the biological tissue.

Lipid Magnet

Compositions of the disclosure for use in clearing a biological sample of lipids are referred to herein as "lipid magnets."

Compositions of the disclosure, in certain embodiments, comprise one or more detergents and/or surfactants. In one aspect, the disclosure provides a composition comprising sodium dodecyl sulfate (SDS). In additional embodiments, the disclosure provides that the composition further comprises one or more components selected from the group consisting of Triton X-100, Tween-20, SB3-14, and sodium chloride. In a further aspect, the disclosure provides that the composition comprises SDS and one or more components selected from the group consisting of Triton X-100, Tween-20, SB3-14, and calcium chloride.

In another aspect, the disclosure contemplates a composition comprising SDS and sodium deoxycholate. In additional embodiments, the disclosure provides that the composition further comprises one or more components selected from the group consisting of Triton X-100, Tween-20, SB3-14, and sodium chloride. In a further aspect, the disclosure provides that the composition comprises SDS, sodium deoxycholate, and one or more components selected from the group consisting of Triton X-100, Tween-20, SB3-14, and calcium chloride.

Detergents that may be used in a composition of the disclosure include those that are anionic, cationic, non-ionic, zwitterionic and non-detergent sulfobetaines.

A surfactant is a compound that lowers the surface tension (or interfacial tension) between two liquids or between a liquid and a solid. Surfactants are usually organic compounds that are amphiphilic, meaning they contain both hydrophobic groups (their tails) and hydrophilic groups (their heads). Therefore, a surfactant molecule contains both a water insoluble (or oil soluble component) and a water soluble component. Surfactant molecules migrate to the water surface, where the insoluble hydrophobic group may extend out of the bulk water phase, either into the air or, if water is mixed with an oil, into the oil phase, while the water soluble head group remains in the water phase. This alignment and aggregation of surfactant molecules at the surface acts to alter the surface properties of water at the water/air or water/oil interface.

The concentration at which surfactants begin to form micelle is known as the critical micelle concentration (CMC). When micelles form in water, their tails form a core that can encapsulate an oil droplet, and their (ionic/polar) heads form an outer shell that maintains favorable contact with water. When surfactants assemble in oil, the aggregate is referred to as a reverse micelle. In a reverse micelle, the heads are in the core and the tails maintain favorable contact with oil. Like detergents, surfactants are often classified into groups including anionic, cationic, non-ionic, and zwitterionic (dual charge).

In various embodiments, the detergent/surfactant is selected from the group consisting of Chenodeoxycholic acid, Choleate sodium salt, Cholic acid, Cholic acid sodium salt, Deoxycholic acid, Deoxycholic acid sodium salt, Glycocholic acid hydrate, Glycocholic acid sodium salt hydrate, Lauroylsarcosine, Lauroylsarcosine sodium salt, Lithium dodecyl sulfate, Sodium dodecyl sulfate (SDS), Sodium deoxycholate monohydrate, Taurochenodeoxycholic acid sodium salt, Taurocholic acid sodium salt hydrate, Taurodeoxycholic acid sodium salt monohydrate, Tauroursodeoxycholate sodium salt, Ursodeoxycholic acid, Hexadecyltrimethyl ammonium bromide, TTAB, Trimethyltetradecylammonium bromide, APO-10, Dimethyldecylphosphine oxide, Big CHAP Deoxy, deoxyBigCHAP, Brij® 35, Brij 35 P, Brij 58, CYMAL-1®, Cyclohexylmethyl-β-D-maltoside, CYMAL-2®, Cyclohexylmethyl-β-D-maltoside, CYMAL-5®, Cyclohexylmethyl-β-D-maltoside, CYMAL-6®, Cyclohexylmethyl-β-D-maltoside, Decanoylsucrose, Sucrose monodecanoate, Decyl β-D-glucopyranoside, Decyl β-D-maltopyranoside, Decyl β-D-1-thiomaltopyranoside, Digitonin, Dodecanoylsucrose, Sucrose monolaurate, Dodecyl β-D-glucopyranoside, Dodecyl β-D-maltoside, Genapol® C-100, Genapol X-080, Genapol X-100, HECAMEG, Methyl 6-O—(N-heptylcarbamoyl)-β-D-glucopyranoside Heptyl-D-glucopyranoside, Heptyl β-D-thioglucopyranoside, Hexadecyl β-D-maltoside, Hexyl β-D-glucopyranoside, Igepal® CA-630, MEGA-10, Decanoyl-methylglucamine, MEGA-8, Octanoyl-methylglucamine, MEGA-9, Nonanoyl-methylglucamine, Nonaethylene glycol monododecyl ether, Nonidet™ P 40 Substitute, Nonyl β-D-glucopyranoside, Nonyl β-D-1-thiomaltoside, Octaethylene glycol monododecyl ether, Octyl β-D-1-thioglucopyranoside, Octyl β-D-maltoside, Octyl-β-D-glucopyranoside, Pluronic® F-127, Pluronic F-68, Polysorbate® 20 (see also Tween® 20), Polysorbate 80 (see also Tween® 80), Saponin, Thesit®, Triton® X-100, Triton X-100 reduced, Triton X-114, Tween® 20, Tween 40, Tween 80, Undecyl β-D-maltoside, ASB 14-4, ASB C7BzO, 3-(4-Heptyl) phenyl 3-hydroxy propyl) dimethylammonio propane sulfonate, ASB-14, Amidosulfobetaine-14, 3-[N,N-Dimethyl (3-myristoylaminopropyl)ammonio]propanesulfonate, ASB-C8Ø, 3-{N,N-Dimethyl-N-[3-(4-octylbenzoylamino) propyl] ammonio}propanesulfonate, CHAPS, CHAPSO, DDMAB, EMPIGEN® BB detergent, SB3-8, Dimethyloctylammonio propanesulfonate, SB3-10, Decyldimethylammonio propanesulfonate, SB3-12, Dodecyl-N,dimethyl-3-ammonio-1-propanesulfonate, SB3-14, Dimethylmyristylammonio propanesulfonate, SB3-16, Dimethylpalmitylammonio propanesulfonate, SB3-18, Dimethyloctadecylammonio propanesulfonate, NDSB 195, Dimethylethylammoniumpropane sulfonate, NDSB 211, Dimethyl-(2-hydroxyethyl)-(3-sulfopropyl)ammonium NDSB 221, 3-(1-Methylpyridinium)-1-propane sulfonate, and NDSB 256-4T, 3-(4-tert-Butyl-1-pyridinio)-1-propanesulfonate, Triton™ X-100, sodium cholate, sodium deoxycholate (SDC), N-Lauroylsarcosine, lauryldimethylamine-oxide (LDAO), cetyltrimethylammoniumbromide (CTAB), and Bis(2-ethylhexyl)sulfosuccinate.

In a specific embodiment, the disclosure provides a composition comprising sodium dodecyl sulfate (SDS), 3-(N,N-Dimethylmyristylammonio)propanesulfonate (SB3-14), Tween® 20, Triton™ X-100, sodium deoxycholate, and a salt.

In general, the amount of detergent and/or surfactant present in a composition of the disclosure is from about 0.01% to about 10%. In various embodiments, the amount of detergent and/or surfactant present in a composition of the disclosure is from about 0.01% to about 9%, or from about 0.01% to about 8%, or from about 0.01% to about 7%, or from about 0.01% to about 6%, or from about 0.01% to about 5%, or from about 0.01% to about 4%, or from about 0.01% to about 3%, or from about 0.01% to about 2%, or from about 0.01% to about 1%, or from about 0.01% to about 0.5%, or from about 0.01% to about 0.1%, or from about 1% to about 10%, or from about 1% to about 9%, or from about 1% to about 8%, or from about 1% to about 7%, or from about 1% to about 6%, or from about 1% to about 5%, or from about 1% to about 4%, or from about 1% to about 3%, or from about 1% to about 2%. In further embodiments, the amount of detergent and/or surfactant present in a composition of the disclosure is about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, or more.

In specific embodiments, the amount of SDS in the composition is from about 1% to about 10% (weight:volume). In some embodiments, the amount of SDS in the composition is from about 1% to about 5%. In one embodiment, the amount of SDS in the composition is about 5%. In further embodiments, the amount of SDS in the composition is about 1%, about 2%, about 3%, about 4%, about 5%, about 6%, about 7%, about 8%, about 9%, or about 10%. In still further embodiments, the amount of SDS in the composition is at least about 1%, at least about 2%, at least about 3%, at least about 4%, at least about 5%, at least about 6%, at least about 7%, at least about 8%, or at least about 9%.

In specific embodiments, the amount of SB3-14 in the composition is from about 0.03% to about 3% (weight:volume). In some embodiments, the amount of SB3-14 in the composition is from about 0.05% to about 1%. In one embodiment, the amount of SB3-14 in the composition is about 0.1%. In further embodiments, the amount of SB3-14 in the composition is about 0.03%, about 0.05%, about 0.1%, about 0.2%, about 0.5%, about 0.8%, about 1%, about 1.5%, about 2%, or about 3%. In still further embodiments, the amount of SB3-14 in the composition is at least about 0.03%, at least about 0.05%, at least about 0.1%, at least about 0.2%, at least about 0.5%, at least about 0.8%, at least about 1%, at least about 1.5%, or at least about 2%.

In further embodiments, the amount of Tween® 20 in the composition is from about 0.3% to about 3% (weight:volume). In some embodiments, the amount of Tween® 20 in the composition is from about 0.5% to about 2%. In one embodiment, the amount of Tween® 20 in the composition is about 1%. In further embodiments, the amount of Tween® 20 in the composition is about 0.3%, about 0.5%, about 0.7%, about 0.8%, about 0.9%, about 1%, about 1.3%, about 1.5%, about 2%, about 2.5%, or about 3%. In still further embodiments, the amount of Tween® 20 in the composition is at least about 0.3%, at least about 0.5%, at least about 0.7%, at least about 0.8%, at least about 0.9%, at least about 1%, at least about 1.3%, at least about 1.5%, at least about 2%, or at least about 2.5%.

In further embodiments, the amount of Triton™ X-100 in the composition is from about 0.3% to about 3% (weight:volume). In some embodiments, the amount of Triton™ X-100 in the composition is from about 0.5% to about 2%. In one embodiment, the amount of Triton™ X-100 in the composition is about 1%. In further embodiments, the amount of Triton™ X-100 in the composition is about 0.3%, about 0.5%, about 0.7%, about 0.8%, about 0.9%, about 1%, about 1.3%, about 1.5%, about 2%, about 2.5%, or about 3%. In still further embodiments, the amount of Triton™ X-100 in the composition is at least about 0.3%, at least about 0.5%, at least about 0.7%, at least about 0.8%, at least about 0.9%, at least about 1%, at least about 1.3%, at least about 1.5%, at least about 2%, or at least about 2.5%.

In further embodiments, the amount of sodium deoxycholate in the composition is from about 0.1% to about 1% (weight:volume). In some embodiments, the amount of sodium deoxycholate in the composition is from about 0.2% to about 0.7%. In one embodiment, the amount of sodium deoxycholate in the composition is about 0.5%. In further embodiments, the amount of sodium deoxycholate in the composition is about 0.1%, about 0.2%, about 0.3%, about 0.4%, about 0.5%, about 0.6%, about 0.7%, about 0.8%, about 0.9%, or about 1%. In still further embodiments, the amount of sodium deoxycholate in the composition is at least about 0.1%, at least about 0.2%, at least about 0.3%, at least about 0.4%, at least about 0.5%, at least about 0.6%, at least about 0.7%, at least about 0.8%, or at least about 0.9%.

In some embodiments, the composition further comprises a salt such as sodium chloride. The concentration of salt in the composition is from about 50 mM to about 500 mM. In further embodiments, the concentration of salt in the composition is from about 50 mM to about 400 mM, or from about 50 mM to about 300 mM, or from about 50 mM to about 200 mM, or from about 60 mM to about 400 mM, or from about 60 mM to about 300 mM, or from about 60 mM to about 200 mM, or from about 70 mM to about 400 mM, or from about 70 mM to about 300 mM, or from about 70 mM to about 200 mM, or from about 80 mM to about 400 mM, or from about 80 mM to about 300 mM, or from about 80 mM to about 200 mM, or from about 90 mM to about 400 mM, or from about 90 mM to about 300 mM, or from about 90 mM to about 200 mM, or from about 100 mM to about 400 mM, or from about 100 mM to about 300 mM, or from about 100 mM to about 200 mM. In still further embodiments, the concentration of salt in the composition is at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, at least about 150 mM, at least about 160 mM, at least about 170 mM, at least about 180 mM, at least about 190 mM, or at least about 200 mM. In additional embodiments, the concentration of salt in the composition is about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, or about 200 mM or more.

The pH of the composition is, in various embodiments, from about 6.5 to about 9. In additional embodiments, the pH of the composition is from about 7 to about 8.5, or from about 7.5 to about 8.5, or from about 7 to about 8, or at least 7, at least 7.5, at least 8, or at least 8.5. In further embodiments, the pH of the composition is 7, 7.5, 8, 8.3, 8.4, 8.5, 8.6, 8.7, 8.8, 8.9, or 9.

In some embodiments, the composition comprises phospholipase A2 (PLA2). In some embodiments, the composition further comprises phospholipase A2 (PLA2). In embodiments that comprise PLA2, the disclosure contemplates that from about 1 to about 50 units of PLA2 is used. In further embodiments, from about 10 to about 50 units of PLA2 is used, and in still further embodiments, from about 20 to about 40 units of PLA2 is used. In one embodiment, about 18 units of PLA2 is used, and in another embodiment, about 36 units of PLA2 is used.

In some embodiments, the composition does not comprise boric acid. In some embodiments, the composition does not comprise urea.

Thus, in one embodiment, the composition comprises 5% sodium dodecyl sulfate (SDS), 0.1% 3-(N,N-Dimethylmyristylammonio)propanesulfonate (SB3-14), 1% Tween® 20, 1% Triton™ X-100, 0.5% sodium deoxycholate, and 150 mM NaCl. In another embodiment, the composition comprises 5% sodium dodecyl sulfate (SDS), 0.1% 3-(N,N-Dimethylmyristylammonio)propanesulfonate (SB3-14), 1% Tween® 20, 1% Triton™ X-100, 0.5% sodium deoxycholate, and 150 mM $CaCl_2$.

Optical Clearing Methods

The method of clearing a biological sample comprises embedding/fixing the biological sample and perfusing/clearing the biological sample. In a further embodiments, the biological sample is prepared for imaging analysis. In yet a further embodiment, the biological sample is subjected to immunohistochemical (IHC) analysis.

Embedding/Fixing Step

The solution used to embed/fix the biological sample of interest comprises acrylamide and a fixative. Types of fixatives useful in the methods of the disclosure are generally known in the art and include without limitation paraformaldehyde (PFA), formalin, Zenker's fixative, Helly's fixative, B-5 fixative, Bouin's solution, Hollande's, Gendre's solution, Clarke's solution, Carnoy's solution, Methacarn, and Formol acetic alcohol. The embedding/fixing solution further comprises, in some embodiments, saponin.

Concentrations of each of the components of the embedding/fixing solution can be determined empirically depending on the application, but in general is as follows. Acrylamide is used at a final concentration of from about 2% to about 10%, or from about 3% to about 8%, or from about 4% to about 6%. In various embodiments, the acrylamide is used at a final concentration of at least about 2%, at least about 3%, at least about 4%, at least about 5%, at least about 6%, at least about 7%, at least about 8%, at least about 9% or at least about 10%. In further embodiments, the final concentration of acrylamide in the embedding/fixing solution is 2%, 3%, 4%, 5%, 6%, 7%, 8%, 9% or 10%.

The concentration of fixative in the embedding/fixing solution will depend on the particular fixative that is chosen, but will in general be used at a final concentration of from about 2% to about 10%, or from about 3% to about 8%, or from about 4% to about 6%. In various embodiments, the acrylamide is used at a final concentration of at least about 2%, at least about 3%, at least about 4%, at least about 5%, at least about 6%, at least about 7%, at least about 8%, at least about 9% or at least about 10%. In further embodiments, the final concentration of acrylamide in the embedding/fixing solution is 2%, 3%, 4%, 5%, 6%, 7%, 8%, 9% or 10%.

In embodiments in which saponin is used, the disclosure contemplates that the saponin is used at a concentration of from about 0.01% to about 1%, or from about 0.01% to about 0.08%, or from about 0.02% to about 0.05%. In one embodiment, the saponin concentration in the embedding/fixing solution is 0.05%.

Once obtained, the biological sample is contacted with the embedding/fixing solution in a vessel that is protected from the light and placed on ice. The volume of embedding/fixing solution to be used is approximately 2 to 5 times the volume of the biological sample.

Next, the vessel containing the embedding/fixing solution and the biological sample is place at 4° C. with gentle agitation. Care should be taken not to agitate/shake the vessel too much so as to avoid damage to the tissue.

The length of time that the biological sample is kept in contact with the embedding/fixing solution depends on various factors, including the source of the biological sample and how effective the perfusing of the biological sample is expected to be.

For a biological sample that is easily perfused such as, without limitation, small intestine, approximately 2 or 3 days is a sufficient time for the biological sample to be left in contact with the embedding/fixing solution.

For a biological sample that is less easily perfused (such as, without limitation, liver, heart, kidney, and muscle), the biological sample is kept in contact with the embedding/fixing solution for about 3 to 5 days. The 3 to 5 day time period is also recommended for human samples that have already been fixed, and samples from larger species such as rat and pig. For a denser organ, and samples from larger-than-murine species, it is also beneficial to use saponin in order to require a shorter incubation time. Saponin can cause bubbles to form in the tissue, however, so proper care must be taken to avoid these issues.

In some embodiments, a perfusion device as depicted in FIGS. 8A-8E is used for fixation in acrylamide/tissue stabilization. In some embodiments, once a tissue sample is floating in gel, a vacuum is applied to create a negative pressure to speed perfusion of gel into sample and remove air bubbles in sample.

Perfusing/Clearing Step

After the sample has been embedded into the gel according to the disclosure, lipids are removed using a high-pressure perfusion system. Use of the acrylamide-based gel is useful because it does not bind the lipids, thus allowing their removal in subsequent step(s).

The perfusion system is, in some embodiments, a pipe shaped chamber that allows a high-pressure flow from a water circulator to shoot the "lipid magnet" composition through a biological sample, thus delipidating the biological sample.

In some embodiments, the chamber is square such that perfusion liquid is forced through the sample using a temperature-controlled impeller pump (see FIGS. 8A-8F). The perfusion chamber includes a fluid inlet coupling and fluid outlet coupling. The chamber is configured to allow for stable flow of the perfusion liquid (e.g., a laminarized flow), through the chamber and in particular through the sample, instead of around the sample. The sample, which may be positioned centrally within the chamber is thus exposed, evenly, to the perfusion liquid, as a treatment before imaging. The chamber configuration allows for a transparent top and can be implemented as a multi-well chamber assembly, which may allow for use of a variety of interchangeable perfusion adaptors or specialized chamber features.

The lipid magnet composition, in various embodiments, further comprises PLA2. In some embodiments, the lipid magnet composition consists essentially of PLA2. In further embodiments, the lipid magnet composition consists of PLA2 and a buffer. In still further embodiments, the lipid magnet composition comprises PLA2.

In embodiments in which PLA2 is utilized, the disclosure contemplates that, in some embodiments, the PLA2 is used in a composition comprising 1% sodium deoxycholate in PBS, $CaCl_2$, and 18 units of PLA2 at pH 8.0.

In some embodiments, a peristaltic pump is used to perfuse a buffer from the left cardiac ventricle of an animal, followed by perfusing an ice-cold fixing solution (such as, without limitation, a paraformaldehyde-buffer solution), so that the animal is systemically fixed.

Additional methods related to perfusing a tissue are known in the art, and are contemplated herein.

Preparing the Sample for Imaging/Refractive Index Matching

To prepare the sample for imaging, the washed, cleared sample is contacted with 2'2'-Thiodiethanol (TDE). TDE has been utilized at different concentrations to clear extremely thick slices of whole mount tissues and cells. TDE is advantageous because at different concentrations one can very accurately adjust the refractive index of the sample in a linear fashion. This allows versatility unachievable by any of these other techniques listed. The light transmittance with TDE is much higher than glycerol, sucrose, and BABB. TDE also maintains fluorescent protein signal for prolonged periods of time due to its anti-oxidant effects. A drawback of TDE is that it works most effectively on cells and extremely thin tissue slices; it is also less compatible with antibody labeling.

The sample is contacted with an amount of TDE sufficient to gradually introduce the TDE into the sample to decrease the Maillard reaction and shrinkage/rigidity of tissue. TDE readily diffuses through lipid membranes so without the lipids the TDE should diffuse through the tissue rather fast, however, it is still better to do this process gradually. In one embodiment, the final concentration of TDE in the sample is 25%. In further embodiments, the final concentration of TDE in the sample is about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or higher. In still further embodiments, the final concentration of TDE in the sample is from about 10% to about 90%, or from about 10% to about 85%, or from about 10% to about 80%, or from about 10% to about 70%, or from about 10% to about 60%, or from about 10% to about 50%, or from about 10% to about 40%, or from about 10% to about 30%, or from about 10% to about 25%, or from about 10% to about 20%, or from about 20% to about 90%, or from about 20% to about 85%, or from about 20% to about 80%, or from about 20% to about 70%, or from about 20% to about 60%, or from about 20% to about 50%, or from about 20% to about 40%, or from about 20% to about 30%, or from about 20% to about 25%.

By way of non-limiting example, a sample is first contacted with about 10% TDE for about 4 hours at room temperature. Next, the sample is washed and contacted again with 10% TDE overnight at room temperature. The 10% TDE is then removed and replaced with about 25% TDE for about four hours at room temperature. Finally, the 25% TDE is removed and replaced with fresh 25% TDE overnight, at room temperature. Alternatively, if the desired final TDE percentage is 80%, a four-hour wash would be performed using 10%, 25%, 50%, and 80% TDE in succession before a final incubation in a full volume of 80% TDE.

Uses

The advantages provided by the methods of the disclosure derive not only from the ability to clear a biological sample, but also provides unprecedented optical/visual resolution as to what can be seen. The ability to delipidate a variety of biological samples while maintaining structural (i.e., protein) integrity in those samples has profound implications for understanding native tissue structure, and by extension, uncovering mechanisms of tissue remodeling, repair and regeneration that were previously unavailable. In short, the methods of the disclosure allow for the connection of tissue structure to tissue function in a fashion that was not previously possible. That is, once the biological sample is optically cleared, there are further opportunities for obtaining insight into tissue physiology and pathophysiology that were previously not possible. Skeletal muscle and bladder will be used to provide important specific guidance on the unanticipated utility of the methods described herein. Such examples, however, will be understood to be non-limiting and simply exemplary.

Skeletal Muscle

The resolution, depth (3D reconstruction of large segments of muscle tissue), and detail in skeletal muscle imaging provided by the present technology are unexpected in view of the art. Specific features that can be easily obtained on whole tissue microscopy that were previously inferred from a series of separate methods and procedures include, but are not limited to, the following.

1. Myofiber diameter—use of the methods described herein allows one to easily obtain measurements in both longitudinal and cross sections;
2. Myofiber orientation (as noted below in detail for bladder, this is a critical aspect in discerning the mechanisms and success of the regenerative response);
3. Neuronal innervation pattern and density;
4. Distribution and stoichiometry of excitation-contraction coupling proteins, as well as proteins involved in activation, force transmission and force production;
5. Sarcomeric length; and
6. Distribution of connective tissue and/or fibrosis.

Moreover, multiple skeletal muscle protein targets can be simultaneously probed in optically cleared tissue. Examples include but are not limited to:

1. Excitation-contraction coupling: acetylcholine receptor clusters (motor endplates; muscle activation), junctophillins, ryanodine receptors, dihydropyridine receptors, calcium channels, ion pumps and transporters, etc.
2. Force production: actin and myosin.
3. Force transmission: desmin, titin, etc.

Physiologically relevant functional measures are critically important. When all of this information is combined with valid functional measures of muscle contraction (i.e., rate, magnitude, duration, threshold/sensitivity—both in vitro and in vivo), it provides for the first time the opportunity to discern previously unavailable and unimaginable insights into mechanism(s) responsible for skeletal muscle impairment, dysfunction, healing, repair, remodeling and regeneration. Further, multiple protein targets can be probed simultaneously on "cleared" skeletal muscle tissue. It is the opportunity to obtain precise quantitative data that connects macroscopic structure and cellular and subcellular expression of key contractile proteins with valid functional measures of muscle contraction that will continue to provide unique mechanistic insight in skeletal muscle pathophysiology, and therefore, point toward new therapeutic strategies for a wide variety of muscle diseases and dysfunctions.

Urinary Bladder

The present techniques can be applied to study bladder function, where the ability to reconstruct the entire bladder in three dimensions (e.g., rodent bladder) provides a unique opportunity to understand structure and function relationships that were previously unobtainable.

By way of example, a series of studies in rats, as well as current data in mice, clearly document a robust proliferative response that results in a complete and functional regeneration of the bladder within 8-12 weeks following removal of 60-80% of the bladder (referred to as subtotal cystectomy). See, e.g., Peyton et al., PLoS One 2012: 7(10) e47414; Burmeister et al., Am J Path 2013 183(5): 1585-95. That is, this phenomenon is associated with normal pressure responses and complete bladder emptying in vivo following bladder regeneration. However, the degree of muscle contractile strength measured on excised bladder tissue from these regenerated bladders clearly shows that the contractile response to receptor-mediated (acetylcholine or carbachol), nonreceptor mediated (KCl) or electrical field stimulation (EFS) are all vastly diminished in the regenerated bladder.

Prior to the development of the current optical clearing technique described herein, one would have to pursue a variety of conventional targets to explain this discontinuity between virtually 100% recovery of function in vivo versus the markedly diminished contractions observed in vitro. Since bladder compliance measured in vivo, as well as the gross architecture of the bladder appeared normal, and furthermore, bladder wall thickness was unchanged, and all three layers of the bladder were verified using available histological and microscopic methodologies, logic dictated that the alterations in contraction in vitro were the product of primary biochemical/physiological changes within the population of smooth muscle cells in the bladder wall that mediate contraction and emptying of the bladder. The possible explanations would include alterations in the expression, activity or function of excitation-contraction coupling proteins (e.g., integral membrane receptors, ion channels, pumps, transporters) or the contractile filaments per se (actin and myosin). However, using methods described herein, it was found that the organization of the myocytes and collagen fibrils distal to the site of original tissue removal (i.e., the suture line) was entirely distinct and discontinuous from that of the rest of the remaining bladder. Since measurement of contraction of strips of tissue in vitro is critically dependent on the orientation of those smooth muscle cells, and moreover, there is no way by looking at the tissue to discern the nature of that orientation prior to studying the tissue in vitro, it is clear that the disconnect between measured force in vitro and measured pressure in vivo (both a product of smooth muscle contraction) was related to the orientation of the smooth muscle cells, not a regeneration-induced alteration in muscle physiology or function per se. That is, prior to the application of the methodology described herein to the study of bladder regeneration, current methods taught away from the true mechanistic basis for the distinction between bladder smooth muscle contraction in vitro and in vivo.

EXAMPLES

Example 1

This example discusses the tissue harvesting and embedding step of the protocol disclosed herein. First, an animal is euthanized according to approved protocol. Cervical dislocation is not performed as it will sever the vasculature to the brain.

Next, the animal is transcardially perfused with 20 mL of 1× ice-cold PBS followed by 20 mL of ice-cold gel/fixative solution. Perfusion can also be performed through the abdominal aorta if isolation of kidneys, liver, and spleen are desired. In addition, organs can be harvested first and then integrated with hydrogel.

Perfusion System

A 2" PVC pipe is capped at both ends and retrofitted with ¼" diameter nozzles at opposite ends. The tube is supported vertically using a chemistry stand and clamp, with the inlet of the tube at the top and the outlet at the bottom. One quarter inch tubing is then connected to both ends of the tube fittings and lead to their desired components of the perfusion system. The water circulator outlet is connected with ¼" hosing to the inlet of a paper based filter chamber that will filter out any contaminants and particulate. The outlet of the first filter is then attached to the inlet of a second filter with ¼" hosing. The outlet of the second filter is then attached to the inlet of the perfusion tube, at the top. The outlet of the perfusion tube is connected to the inlet of the water circulator to complete the system. Optionally, quick-link attachments are utilized in the hosing line between all of the connectors in order to create an easy way to remove the components when necessary. The water circulator used is a thermo adjustable bath that is set at 37-42° Celsius.

Alternatively, and as disclosed herein, perfusion may be carried out using a device according to FIG. 8A-E.

After the samples have been embedded into the gels and have been washed, the samples are loaded into histology paraffin cassettes and placed stack wise in the perfusion tube. The cassettes are aligned perfectly so that the flow of the perfusion is directed equally through the cassettes.

Fixative/Gel Solution

For 400 mL of Hydrogel Monomer Solution:

| Ingredient | Amount to Add | Final Concentration |
| --- | --- | --- |
| Acrylamide (40%) | 40 mL | 4% |
| Bis (2%) | 10 mL | 0.05% |
| VA-044 Initiator | 1 gram | 0.25% |
| 10X PBS | 40 mL | 1X |
| 16% paraformaldehyde (PFA) | 100 mL | 4% |
| dH2O | 210 mL | |
| Saponin (optional) | 200 mg | 0.05% |

Total Volume = 400 mL

The fixative/gel solution should be stored at −20° C. if it is not going to be used right away. Thaw the frozen solution on ice with occasional rolling in gloved hands, or slowly at 4° C. overnight.

The target tissue is then quickly removed from the specimen and rinsed quickly in 1× ice-cold PBS to remove excess blood. The tissue is then transferred into ice-cold gel/fixative solution in an aluminum foil covered 50 mL conical tube, on ice. The volume of gel solution required depends on the size of the sample collected. As a general rule, approximately 3× the volume of the tissue isolated is used in order to waste as little gel solution as possible.

Next, the covered tubes are placed at 4° C. on a rocker for agitation. A shaker is not recommended since this increases the chance for physical damage to the tissue. The sample is allowed to incubate for 2-3 days for tissues that could be rinsed with perfusion. For samples that are much more dense and are not affected by perfusion as much, such as liver, heart, kidney, and muscle, an incubation period of 3-5 days is recommended. This is also recommended for human samples that have been fixed and samples from larger species such as rat and pig. For the denser organs, and samples from larger-than-murine species, it is also beneficial to use saponin in order to require a shorter incubation time, however, saponin can cause bubbles to form in the tissue so proper care must be taken to avoid these issues.

Gel Polymerization

The tubes are taken on ice to a fume hood. Next, the tubes are placed into a desiccator with the caps loosened to allow enough gas exchange to occur. The dessicator is then purged with nitrogen for 5 seconds and the valve is closed. The dessicator valve is then opened and the vacuum is turned on for 10 minutes, allowing the vacuum to remove any air in the tubes. Next, the dessicator valve is closed and the vacuum turned off.

Finally, the nitrogen is turned on while opening the desiccator valve to allow nitrogen to replace the vacuum inside the tubes. With the nitrogen purging the desiccator, the desiccator is lifted up just enough to reach the tubes. The caps of the tubes are then screwed as tightly as possible while keeping the nitrogen purging over the top of the tubes.

The tubes are then moved immediately to 37° C. on a rocker with slight agitation. Use enough agitation to keep the tissue from easily falling to the bottom of the tube. The gel solution is then allowed to completely polymerize over the next two to three hours.

Example 2

This example discusses the tissue clearing and sample preparation for imaging steps of the protocol disclosed herein. First, the gel samples are removed from the tubes and any excess gel is teased away from around the tissue. Then the samples are placed into covered 50 mL conical tubes with 50 mL of wash buffer for two 24-hour periods at 37° C. on an end-over-end rocker. This is to help remove any excess PFA or acrylamide, as well as to help prime the sample for perfusion with the clearing buffer.

The samples are then placed into individual immunohistochemistry (IHC) tissue cassettes, labeled using pencil with what tissue it is. The perfusion chamber and water circulator is then prepared by connecting the hoses and filling the circulator with the clearing buffer.

"Lipid Magnet" Clearing Buffer

This formulation is for 10 liters of a solution.

| Component | Amount to add for 10 Liter batch |
|---|---|
| 5% SDS | 500 g |
| 0.5% Sodium Deoxycholate | 50 g |
| 1% Triton X-100 | 100 mL |
| 1% Tween-20 | 100 mL |
| 0.1% SB3-14 | 10 g |
| 150 mM NaCl or $CaCl_2$ | 87.66 g for NaCl |

Fill to 10 liters with $dH_2O$, then use HCl or NaOH to adjust the pH to 8.5.

The samples are placed into the perfusion chamber, stacked on top of one another in the same direction so that the grating of the chambers matches up. This will help with the flow of the system. The perfusion pump is turned on and is set at 37° C. The samples are then allowed to perfuse until the tissues are completely clear. This can take several days for most tissues. Tissues that are dense, such as kidney and heart, will take approximately 2 weeks to clear. The samples are then removed from the perfusion chamber, placed back into covered 50 mL conical tubes with 50 mL of wash buffer, and placed at 37° C. on an end-over-end rocker for approximately 48 hours.

The samples are then washed for one more 24 hour period in 1×PBS to remove excess detergents from the tissue.

Next, the samples are prepared for imaging. The washed, cleared sample is placed into a new covered 50 mL conical tube and the tissue is covered with approximately 5 mL of 10% TDE for 4 hours at room temperature. The TDE is removed and replaced with fresh 10% TDE, and the tubes are placed upright on a rocker overnight at room temperature.

The 10% TDE is then removed and replaced with enough 25% TDE to cover the tissue (approximately 5 mL), and the tube is left at room temperature for about 4 hours. The TDE is then removed and replaced with clean 25% TDE and left overnight at room temperature on a rocker with the tubes upright. Here, enough TDE is used to fill up the dish that will be used for imaging. For 3.5 cm dishes, about 20 mL is used. For the large dishes you will most likely need 50 mL.

The sample is then mounted for imaging. First, a snake worm is created with the BlueTack that is the same height as the tissue, making sure that there are no cracks. The RI-matched cleared tissue is then placed inside the blue ring, which is then filled with the RI-matched TDE such that the tissue is covered.

Finally, a glass bottomed dish is pressed down firmly on top of the blue snake and sample so that the glass bottom of the dish makes contact with the sample. The sample is now ready for appropriate imaging analysis.

Results

Using the methods as detailed in Examples 1 and 2, high resolution images of tissue were captured. The figures provided herein are exemplary images that demonstrate the level of structural detail that can be acquired on all tissue samples, including those tissues that are millimeters in thickness. The results are unprecedented and provide important details regarding muscle function. In addition, the methods described herein further provide that such experiments can optionally be combined with immunofluorescence/immunohistochemistry.

Figure 1B:
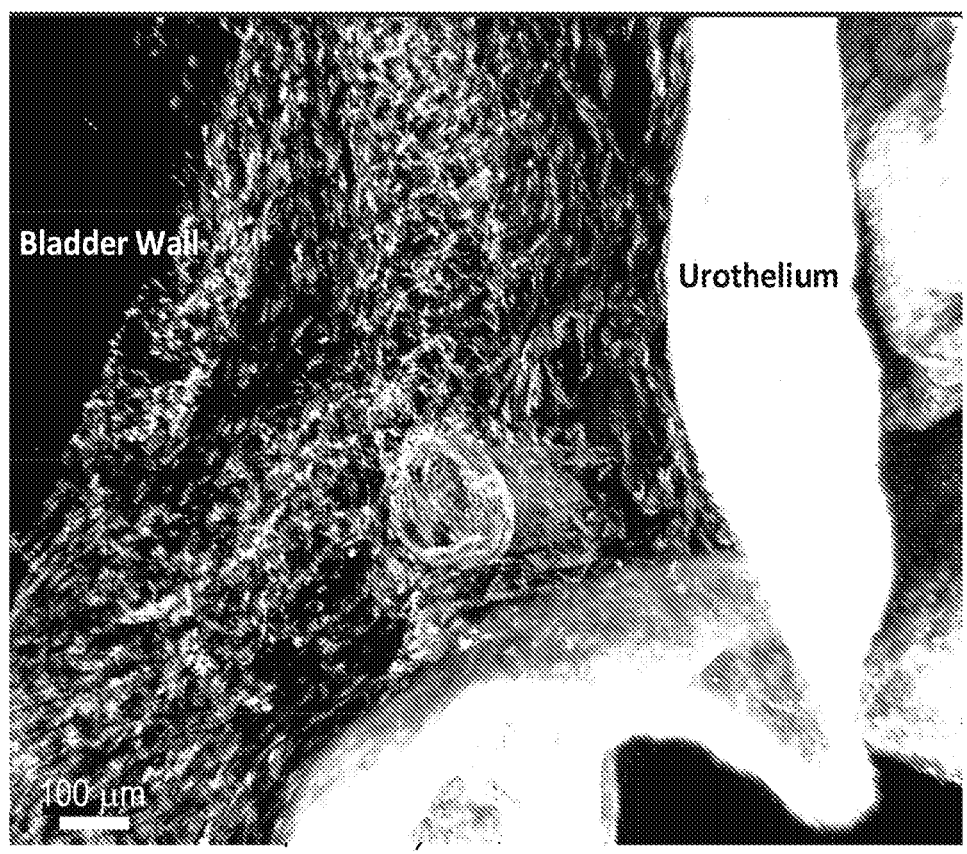
Figure 1C:
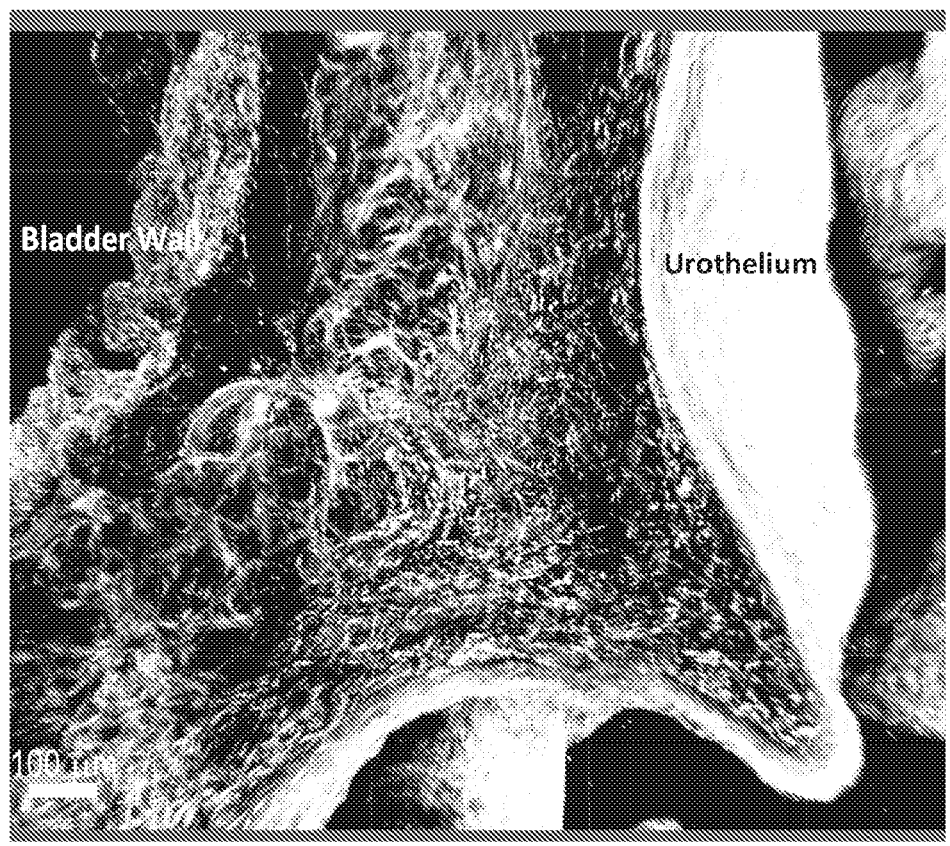

FIG. 1A shows a macroscale image with cellular level resolution of a normal rat bladder obtained from a collagen 1-expressing mouse Note the cellular level resolution of the individual cells (i.e., green (labeled as "urothelium") in the bladder wall. FIG. 1B shows individual cells, while FIG. 1C depicts the fibrillar (e.g., collagen) structures of the bladder wall. The "bladder wall" shown in FIGS. 1A-1C represents the extracellular matrix surrounding the tissue. This ability to image both tissue and external structures, such as the extracellular matrix, are unexpected benefits of the present techniques. Imaging of such external structures—in particular, structures identifiable through second harmonic generation—is not available in conventional techniques where such imaging was not even identified as possible. It is believed that such imaging is available with the present techniques due to the non-destructive nature of the sample treatment. In any event, macroscale images that include second harmonic generation are made available with the present lipid magnet techniques.

Figure 2:
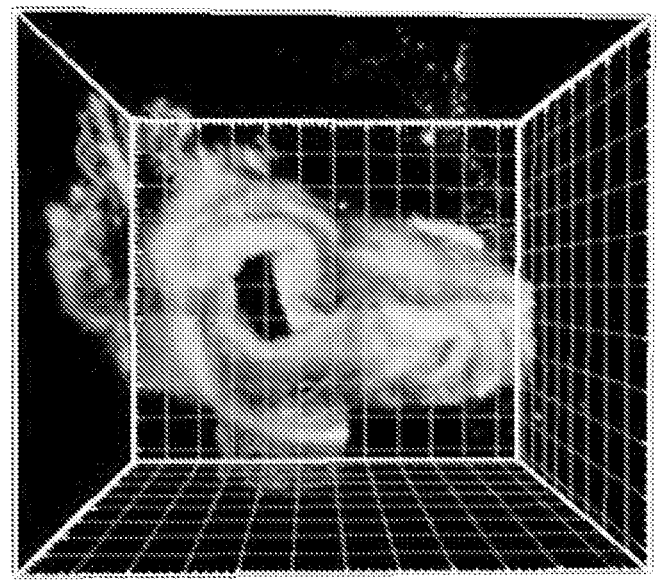
FIG. 2 depicts a macroscale three-dimensional (3D) image of an entire murine bladder. The view is from the top (dome) of the bladder.

FIG. 2 depicts a macroscale three-dimensional (3D) image of an entire murine bladder. As shown, the methods of the disclosure allow for visualization of highly detailed relationships between cells/parenchyma and the connective tissue (fibrillar collagen). This figure makes clear the regular pattern of cells and connective tissue characteristic of the organization observed in the normal/native bladder wall.

Figure 3A:
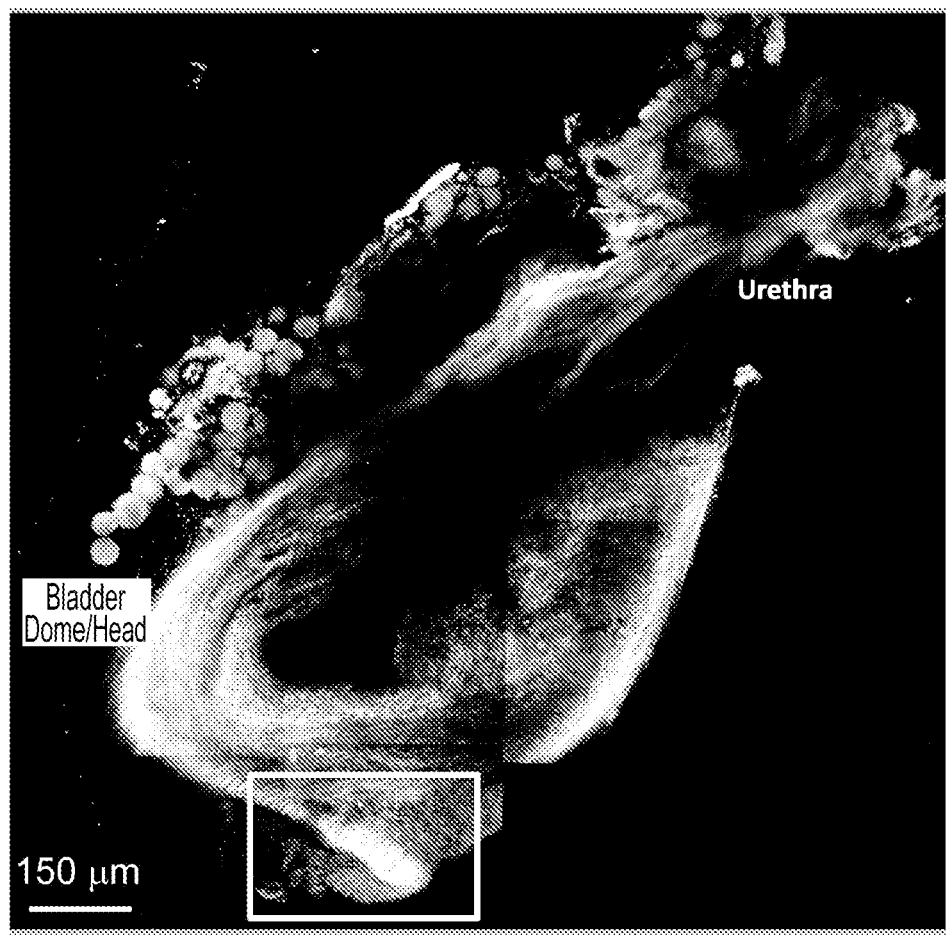
FIGS. 3A and 3B depict a macroscale image of a slice of regenerating bladder 12 weeks after subtotal cystectomy. The orientation is the same as is shown in FIG. 2.
Figure 3B:
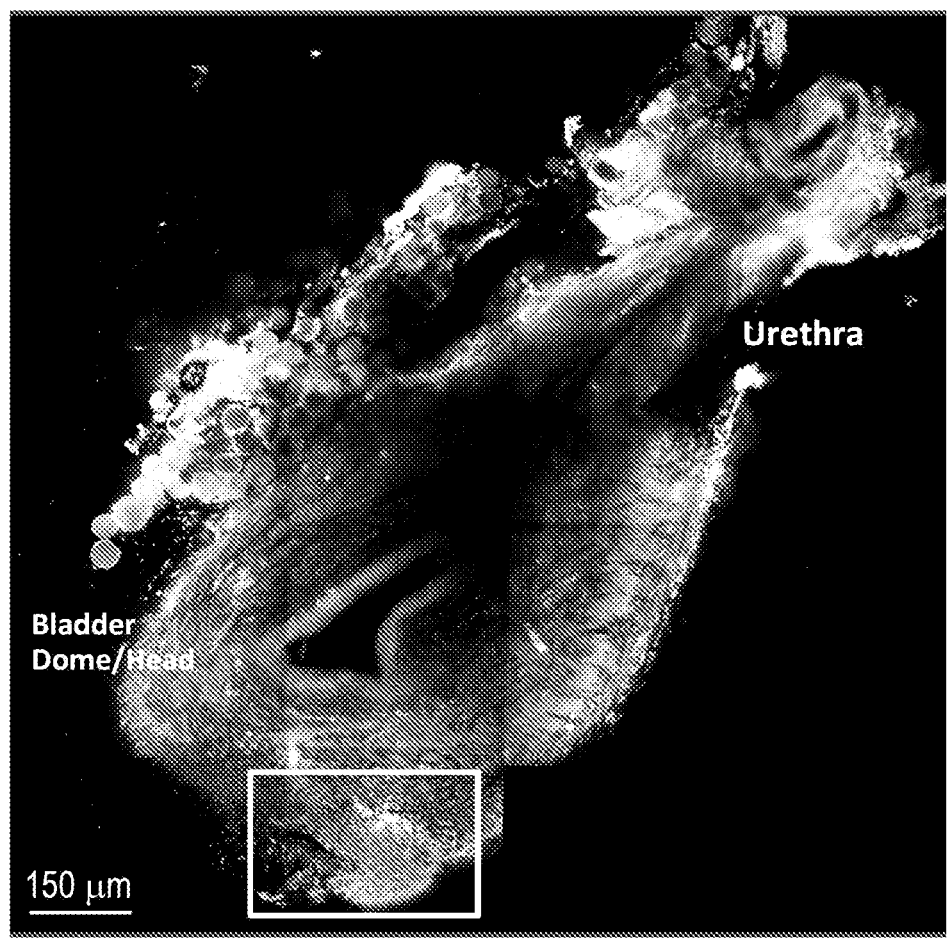

FIGS. 3A and 3B depict a macroscale image of a slice of regenerating bladder 12 weeks after subtotal cystectomy (removal of approximately 60% of the bladder). Note the irregular arrangement and organization of the collagen/fibrillar network at the dome of the bladder following regeneration. This is a key finding that appears to account for the discordance between the normal pressure responses observed in vivo in these animals relative to the much lower than normal contractile responses observed in vitro following stimulation of the smooth muscle cells (i.e., to potassium chloride, electrical field stimulation or acetylcholine).

Figure 4:
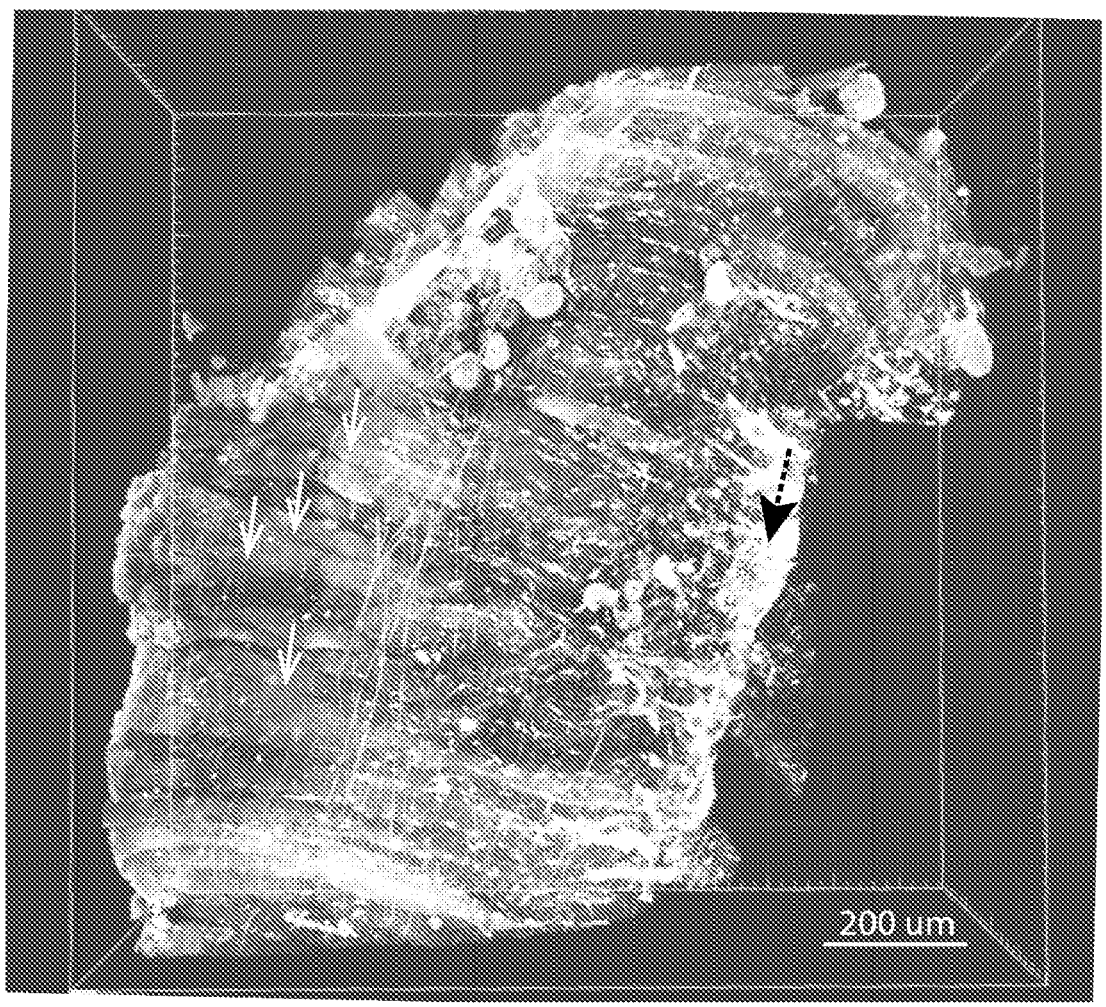
FIG. 4 shows an approximately 5 mm cubed section of mouse tibialis anterior (TA) muscle. Collagen 1 producing cells are highlighted in white. Individual muscle fibers are readily apparent (white arrows) as is a putative inscription site (black arrow).
Figure 5:
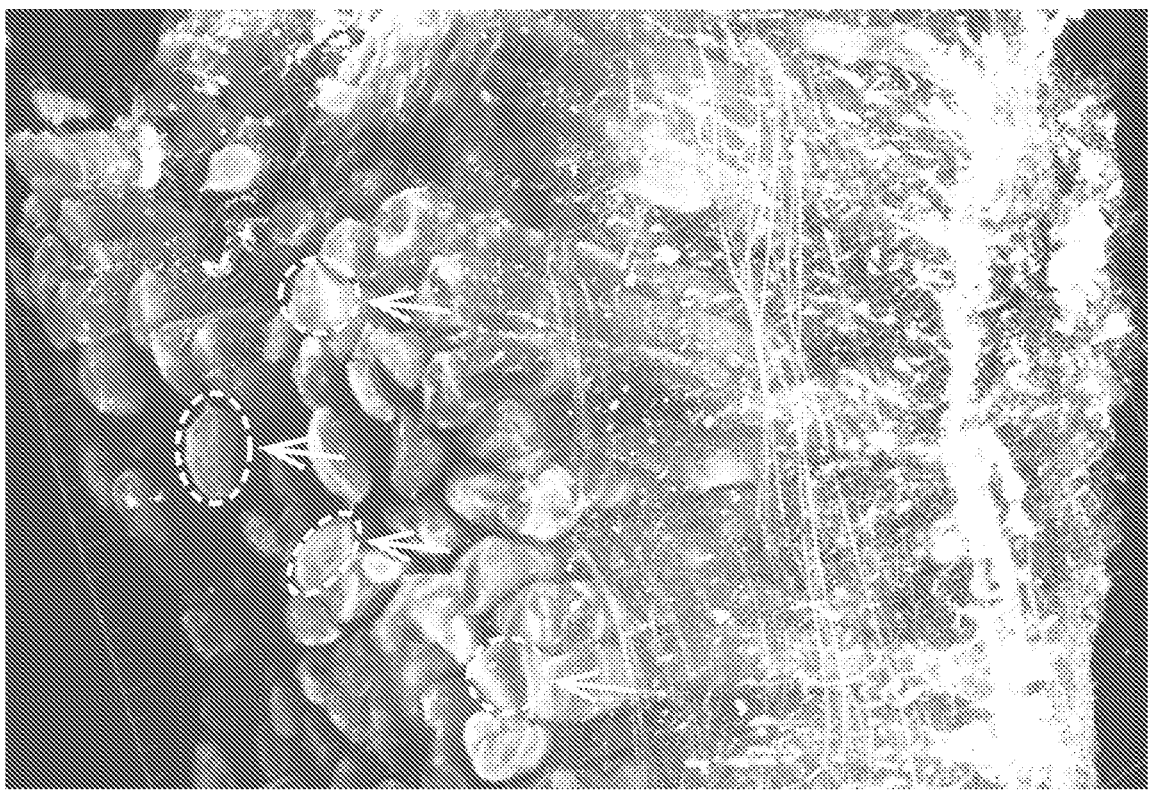
FIG. 5 shows a higher magnification view of the image depicted in FIG. 4. Note that in this panel the individual myofibrils (shown in cross-section and highlighted in dashed circle) are apparently visible in the individual muscle fiber (white arrows).
Figure 6:
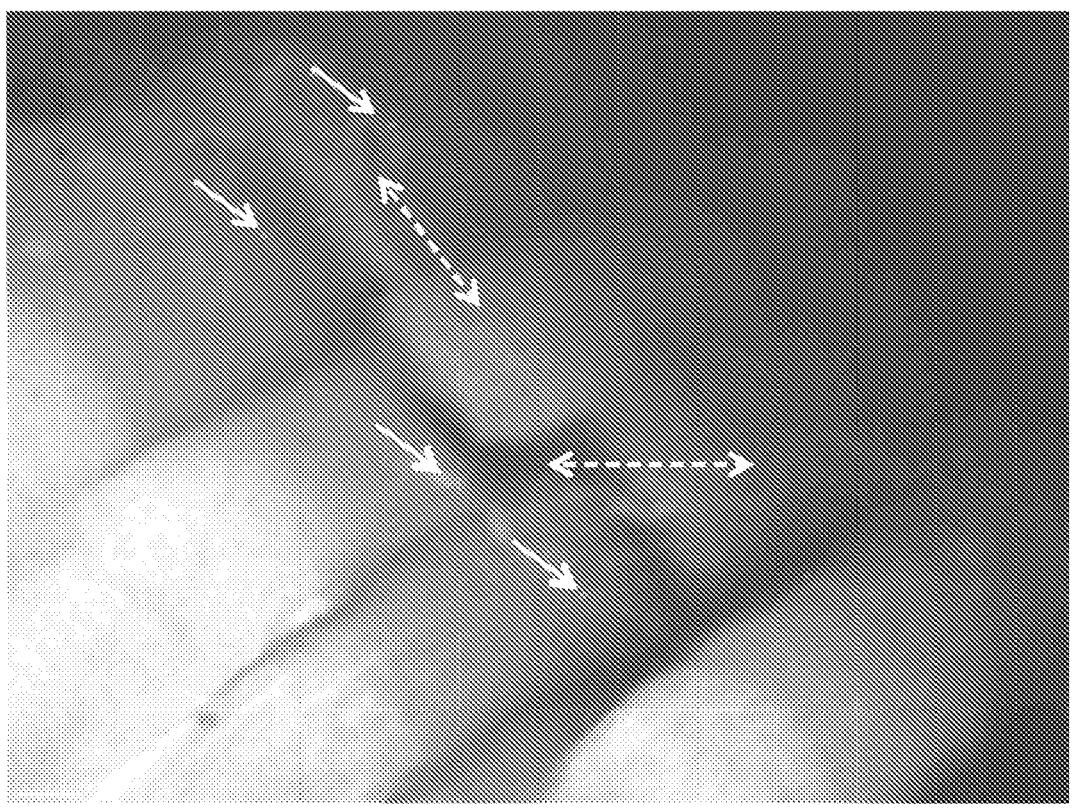
FIG. 6 is an illustration of the ability to discern nerves running alongside the dashed arrows) ramifying across the surface of individual muscle fibers at high resolution. White arrows show putative alpha bungarotoxin staining—indicating sites of motor end plates (MEPs) at the neuromuscular junction.

FIGS. 4 and 5 show an approximately 5 mm cubed section of mouse tibialis anterior (TA) muscle where arrows highlight high-resolution imagery of individual muscle fibers that comprise the TA, demonstrating yet again the ability for the methods herein to preserve native tissue architecture at a millimeter (FIG. 4) and micrometer (FIG. 5) resolution.

Figure 7:
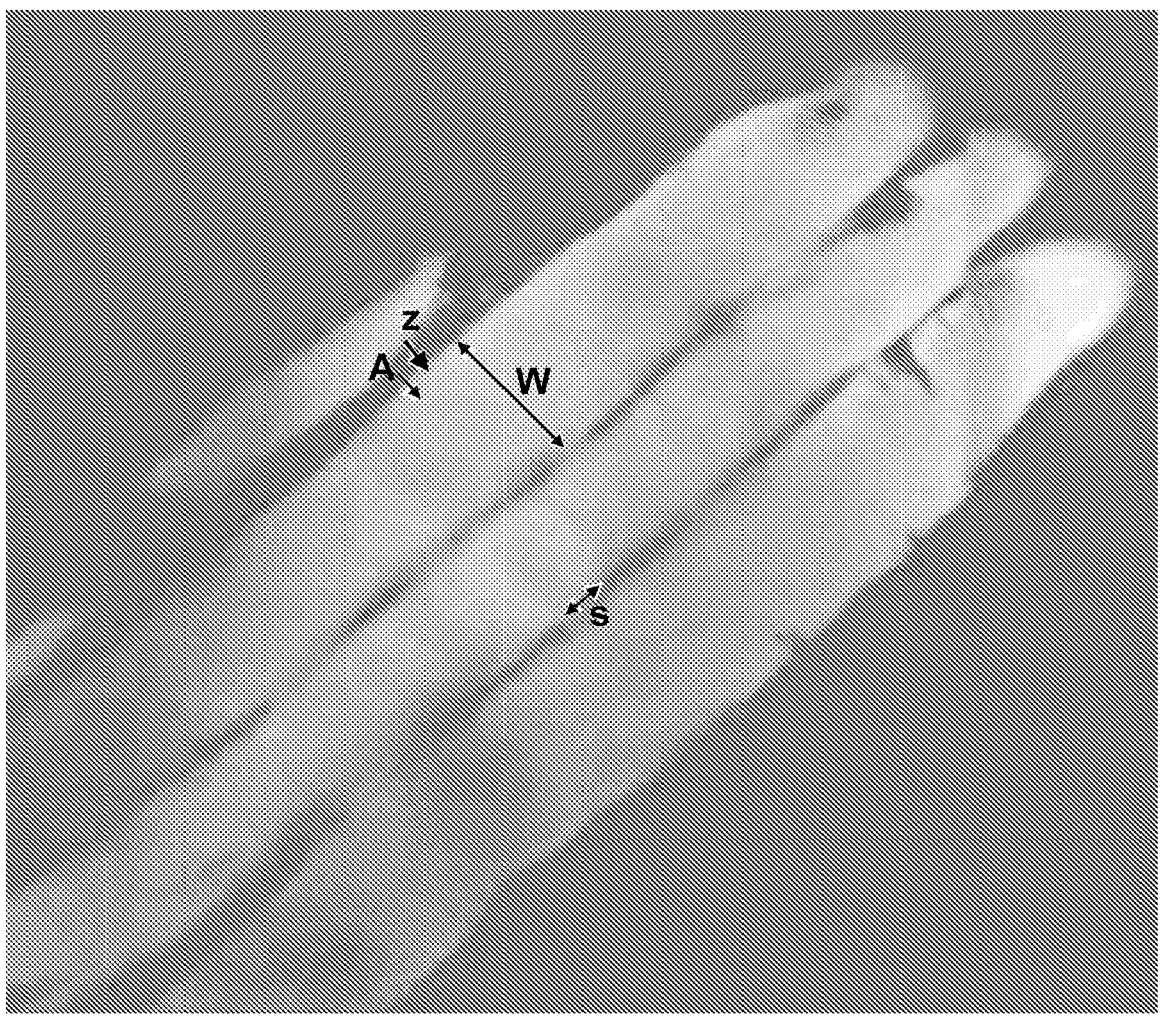
FIG. 7 depicts a high magnification view of individual muscle fibers, showing typical sarcomeric repeats (S). The length and width of the muscle fibers (W) in muscle bundles can easily be determined, as can the characteristics of the sarcomeric repeats.
Figure 8A:
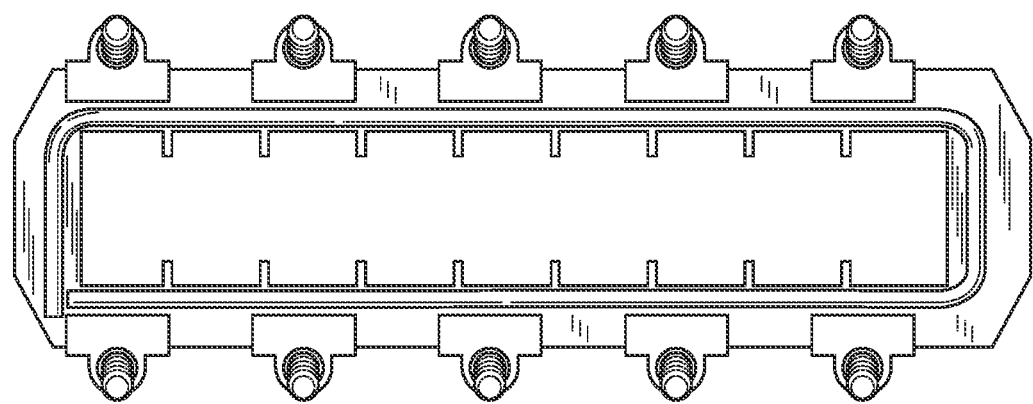
FIGS. 8A-8E depict photographs of a perfusion device contemplated for use according to the methods of the disclosure.
Figure 8B:
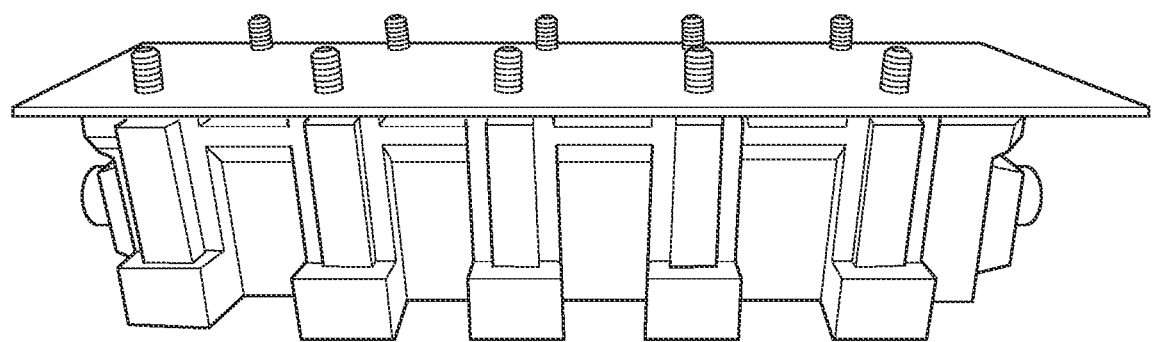
Figure 8C:
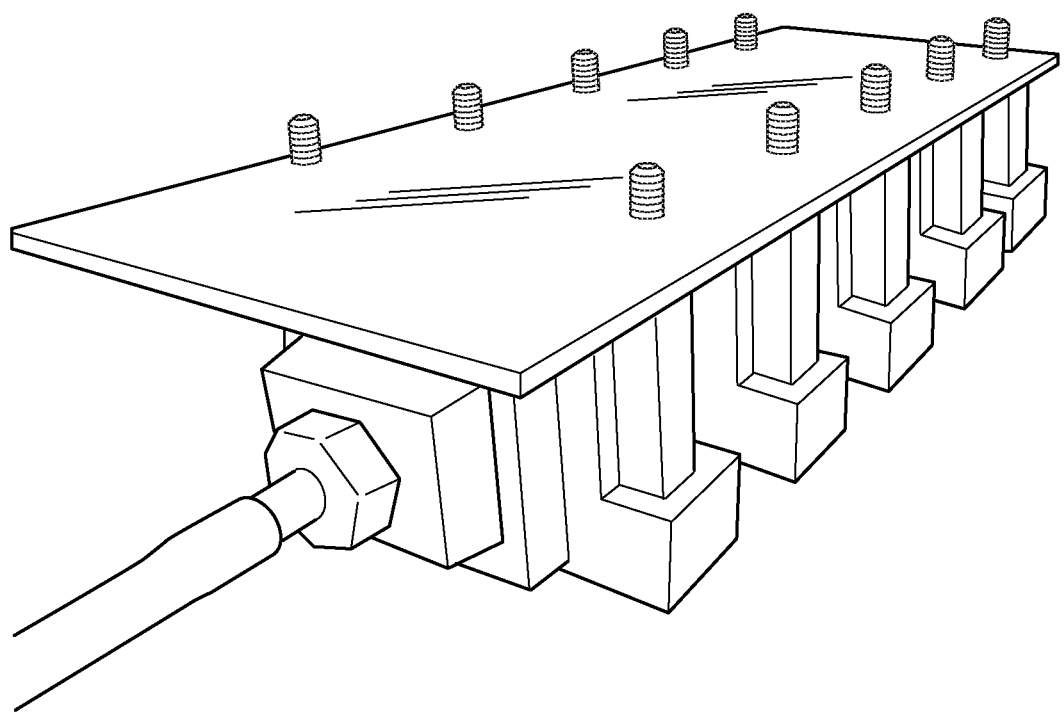
Figure 8D:
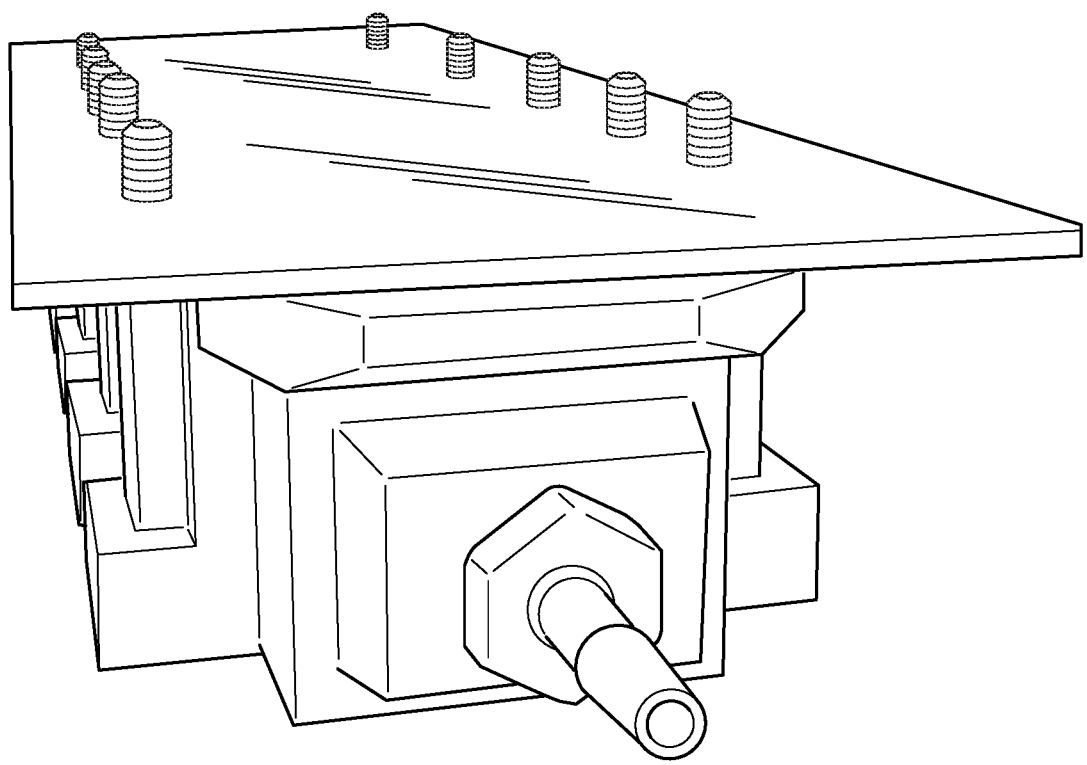
Figure 8E:
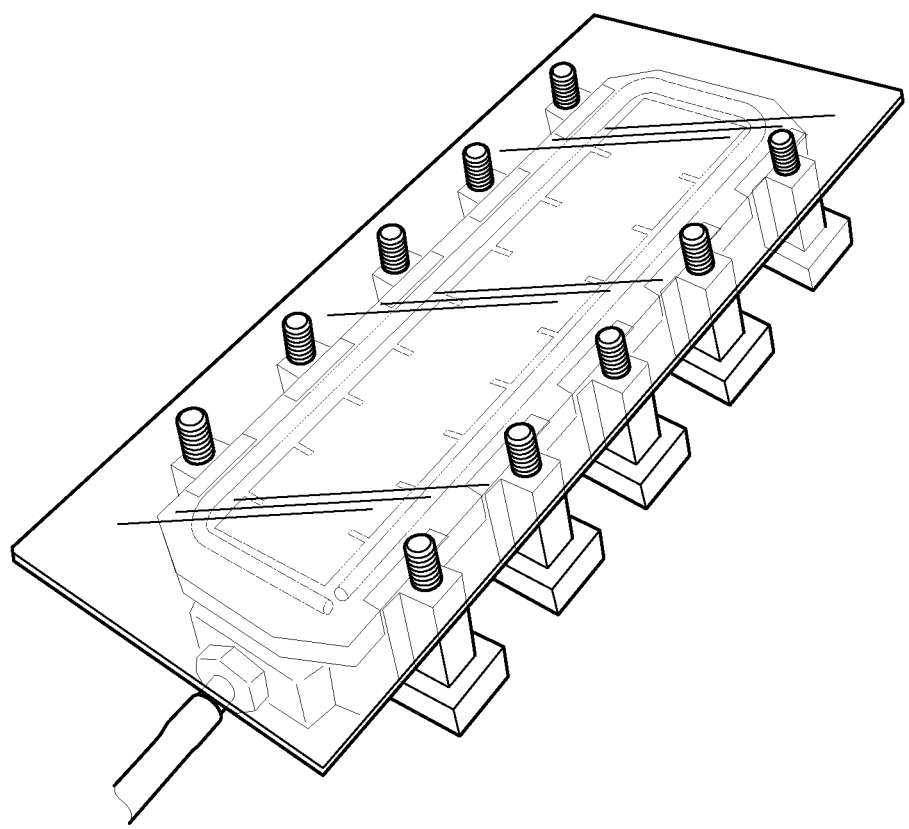

FIG. 7 depicts a high magnification view of individual muscle fibers, showing typical sarcomeric repeats (S). The length and width of the muscle fibers (W) in muscle bundles can easily be determined, as can the characteristics of the sarcomeric repeats. Large scale sampling of numerous fibers in the same muscle bundle, at the same time, will provide much more detail about muscle structure than previously available with much more modest sampling techniques, under harsher preservation conditions. Moreover, the ability to correlate this information with functional measures made on the same muscle (in vitro or in vivo) provides novel insight into muscle structure and function—particularly with respect to muscle regeneration and pathophysiology.

Figure 9:
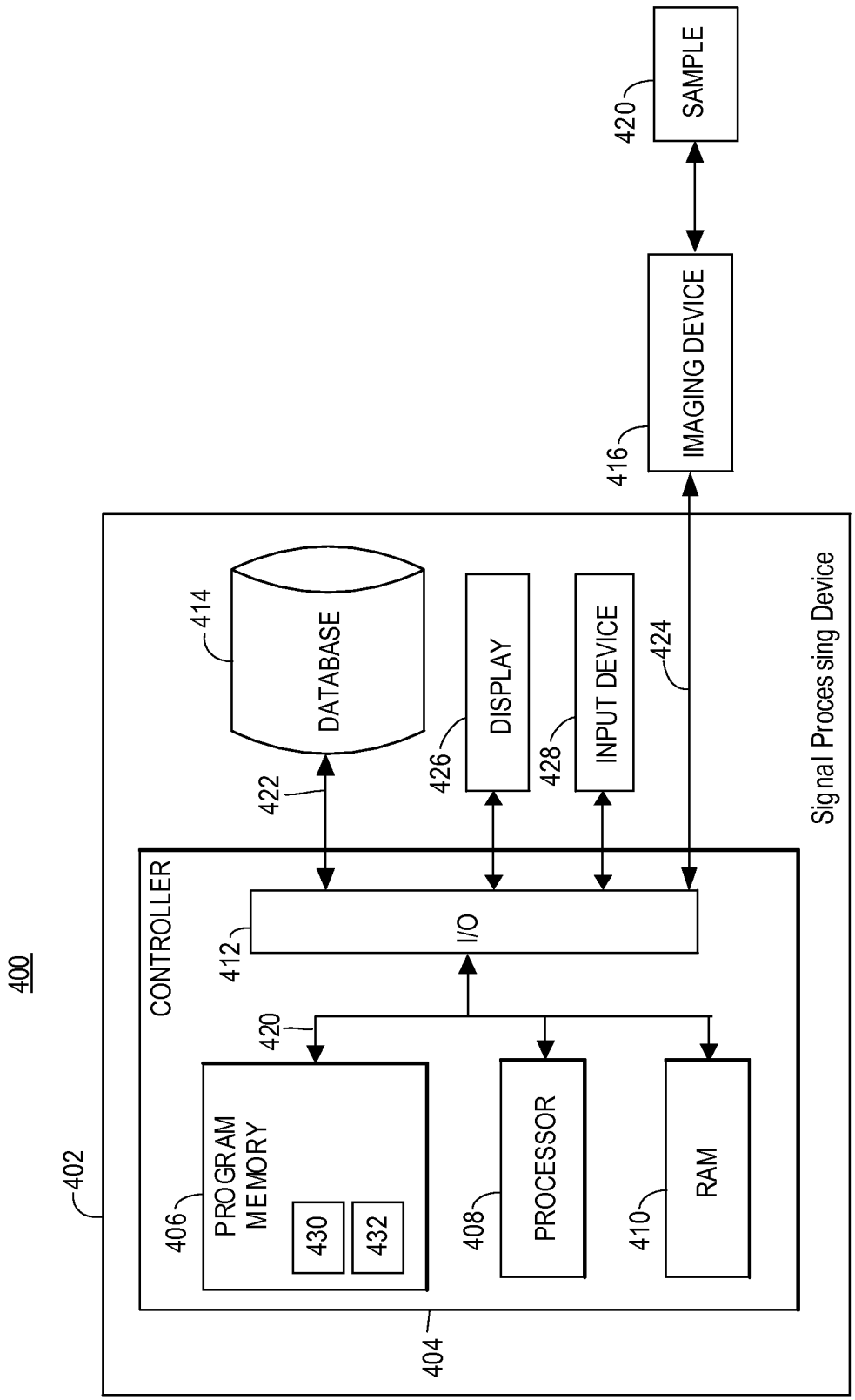
FIG. 9 illustrates a real-time image processing system capable of performing deep tissue imaging and analysis, in accordance with an example.

The present techniques facilitate the generation of much higher quality and much more detailed (to a lower sized feature scale) than available in the prior art. FIG. 9 illustrates an example image processing system 400 capable of performing such deep tissue imaging to construct images that allow for detection of features such as (i) myofiber diameter, (ii) myofiber orientation, (iii) neuronal innervation pattern and density, (iv) distribution and stoichiometry of excitation-contraction coupling proteins, as well as proteins involved in activation, force transmission and force production, (v) sarcomeric length, and (vi) distribution of connective tissue and/or fibrosis, among other features.

FIG. 9 is an example block diagram 400 illustrating the various components used in implementing an example embodiment of the present techniques. A signal processing device 402 (or "signal processor" or "diagnostic device") is configured to collect image data taken from sample or perfusion device 420 via an imaging device 416 (e.g., such as FIGS. 1-7) in accordance with executing the functions of the disclosed embodiments. Such collected image data may be like that depicted in FIGS. 1-7 The signal processing device 402 may have a controller 404 operatively connected to a database 414 via a link 422 connected to an input/output (I/O) circuit 412. It should be noted that, while not shown, additional databases may be linked to the controller 404 in a known manner. The controller 404 includes a program memory 406, one or more processors 408 (may be called microcontrollers or a microprocessors), a random-access memory (RAM) 410, and the input/output (I/O) circuit 412, all of which are interconnected via an address/data bus 420. It should be appreciated that although only one processor 408 is shown, the controller 404 may include multiple microprocessors 408. Similarly, the memory of the controller 404 may include multiple RAMs 810 and multiple program memories 406. Although the I/O circuit 412 is shown as a single block, it should be appreciated that the I/O circuit 412 may include a number of different types of I/O circuits. The RAM(s) 410 and the program memories 406 may be implemented as semiconductor memories, magnetically readable memories, and/or optically readable memories, for example. A link 424, which may include one or more wired and/or wireless (Bluetooth, WLAN, etc.) connections, may operatively connect the controller 404 to the imaging device 416 through the I/O circuit 412. In other examples, the imaging device 416 may be part of the signal processing device 402.

The program memory 406 and/or the RAM 410 may store various applications (i.e., machine readable instructions) for execution by the processor 408. For example, an operating system 430 may generally control the operation of the signal processing device 402 and provide a user interface to the signal processing device 402 to implement image processing operations to produce deep tissue images as discussed herein. The program memory 406 and/or the RAM 410 may also store a variety of subroutines 432 for accessing specific functions of the signal processing device 402. By way of example, and without limitation, the subroutines 432 may include, among other things: a subroutine for collecting image data from the device 416, a subroutine for constructing image data into 3D images of tissues for display on the display 426, a subroutine for allowing uses to interact with the 3D images, e.g., by selectively zooming in on and selecting portions of tissue in the 3D images, for example, to display tissue portions across variation magnification levels, from microscopic, to meso-scale, to macroscale images, a subroutine for identifying one or more features of the tissue from the constructed 3D image data, such as subroutines for automatically determining (i) myofiber diameter, (ii) myofiber orientation, (iii) neuronal innervation pattern and density, (iv) distribution and stoichiometry of excitation-contraction coupling proteins, as well as proteins involved in activation, force transmission and force production, (v) sarcomeric length, and (vi) distribution of connective tissue and/or fibrosis.

The subroutines 432 may also include other subroutines, for example, implementing software keyboard functionality, interfacing with other hardware in the signal processing device 402, etc. The program memory 406 and/or the RAM 410 may further store data related to the configuration and/or operation of the signal processing device 402, and/or related to the operation of the one or more subroutines 432. For example, the data may be data gathered by the device 416, data determined and/or calculated by the processor 408, etc.

In addition to the controller 404, the signal processing device 402 may include other hardware resources. The signal processing device 402 may also include various types of input/output hardware such as a visual display 426 and input device(s) 428 (e.g., keypad, keyboard, etc.). In an embodiment, the display 426 is touch-sensitive, and may cooperate with a software keyboard routine as one of the software routines 432 to accept user input. It may be advantageous for the signal processing device 402 to communicate with a medical treatment device, medical data records storage device, or network (not shown) through any of a number of known networking devices and techniques (e.g., through a commuter network such as a hospital or clinic intranet, the Internet, etc.). For example, the image processing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

The subroutines 432 may include subroutines to provide a graphical user interface (GUI) on the display 426. The GUI (e.g., a MATLAB-based GUI) may be used to depict processing operations to a user to allow a user to monitor such operations and correct, pause, enhance, or otherwise affect, as desired during processing. Either way, the subroutines 432 include instructions for rapidly processing microscopy data (e.g., teravoxel) for 3D reconstruction and analysis using a 3D imaging platform, such as the Bitplane Imaris platform. In this way, the multiphoton imaging may occur on a dedicated computer terminal reserved for the image acquisition process and specific to the particular manufacturer requirements or recommendations, such as a separate 3D imaging processing apparatus coupled to the processing device 402. In other examples, the 3D imaging platform and display may be executed through the subroutines 432 Both open source and proprietary imaging platforms may be implemented in the illustrated configurations. A dedicated 3D platform, such as Bitplane's Imaris offers many advantages to other platforms including the inclusion of multi-resolution data for rapid loading and visualization of tera-voxel datasets (traditionally defined as datasets that comprise more than $10^{12}$ volumetric pixels, here defined as imaging datasets on the order of 100 GB or greater as a rough estimate). The imaging platform is capable of automatically performing image stitching to provide an image that may be manipulated by the user, as the user zooms in and out from a macroscale, to mesa-scale, to microscopic image of the voxel data of tissue data. For example, the imaging platform may be configured to collect images, add channel data, perform dimension changes on the data and recording and registering of coordinates, and perform necessary conversions across images and image magnifications, but compiling the image data and exporting it for display.

Although depicted as separate entities or components in FIG. 9, it is understood that any or all of the signal processing functionality and/or components of the signal processing device 402 may be combined with an imaging device, such as a confocal microscopic tissue image collection device. In this manner, a system 400 may both gather image data about a tissue sample, treated in the perfusion device 420 through the techniques described above, and process the gathered data to identify and analyze one or more features thereof. Also, although depicted as a single component in FIG. 9, the imaging device 416 may include multiple of the same type or different types of imaging device.

The signal processing device 402 may be configured to perform additional functions, e.g., through the subroutines 432. For example, the device 402, may include subroutines that enable quantification of stressor/tensor on image tissue, i.e., allowing for mathematically "tug" on tissue to see how it responds. The device 402 may be coupled to control a microscope of the imaging device 461 to allow for varying Z-axis determinations, i.e., to control the microscope in response to identifying where "nondata" or empty space begin in the sample 420 based on threshold level of such nondata so the microscope will stop collecting data on such nondata and advance to "real data" in the sample 420, based on threshold level of such real data. Hereafter, this concept of differentiating "nondata" from "real data" will be referred to as "Differential Z scanning". Methods provided herein enable one to perform whole-organ imaging of biological tissues. However, traditional microscope controllers are designed to acquire imagery by forming a "bounding box" in three-dimensional space. While relatively user-friendly for scientists analyzing small specimens, using this technique for analyzing whole-organs is largely infeasible at high resolutions necessary for accurately assessing structure-function relationships in tissues owing to the unnecessary collection of "empty images" or nondata acquired in which no tissue is present, thus no fluorescent signal is generated (FIG. 10A). Moreover, time spent acquiring nondata is extremely cost-prohibitive for large organs. Using Differential Z scanning, relevant data is acquired. The device 402 may collect metadata such as (XY position) of where nondata begins and ends to visualize empty spaces but improved throughput if the microscope isn't collecting data on empty spaces other than XY position (FIG. 10B). The device 402 may include subroutines to calculate where each image picture is located in an 3D XYZ space and automatically orient each picture one to another to render a whole or complete visualization of the entire sample in 3D. The device 402 may "stitch" together hundreds to thousands of XYZ images to form the 3D images.

By taking the image data from the device 416 and converting it into stressor-tensor images to calculate/quantitate the mechanical forces that the matrix images provide, this allows for determining better "structure function relationships" in tissue that can be used to better predict which regenerative tissues will work better, based on the image analysis data. The 3D image quality is further enhanced by the differential-Z operation of scanning, where, for example, the device 402 controls a confocal microscope program to allow the microscope of the imaging device 416 to turn on/off, depending on when the microscope "sees" a thresholded amount of signal. Because a large majority of block collected information is nondata or airspace, the differential-Z operation herein allows the microscope to selective avoid collecting image data over this region, reducing data set size and processing time. The device 402, for example, may include subroutines to follow the contour of tissue in the sample 420 and instruct the device 416 to selectively turn on/off accordingly, and once airspace is reached. For example, the device 402 may control the device 416 to effectively turn off image collecting and then zoom forward until the device 416 "sees" tissue again. The amount of signal threshold that used to trigger on/off operation of the image collection may vary. Varying the threshold can be used to control the amount of image noise in "airspace" regions of data collection. Moreover, the threshold can be frequency dependent. For example, in some implementations, the differential z-axis scanning triggers based on the presence of a tissue, while in other examples the scanning triggers based on detection of the extra-cellular matrix (ECM) which is detectable using a wavelength associated with second harmonic generation. In this way, triggering may occur by detecting the presence (or absence) of light at frequencies other than those used in imaging primary tissue, a technique that is particularly useful in imaging tissue having a connective matrix. For example, if the bladder tissue of FIG. 1A is imaged at a primary wavelength (e.g., 870 nm) and the extra cellular matrix surrounding the bladder tissue is imaged at second harmonic generation (i.e., a SHG wavelength of half the primary matrix, 435 nm), the system is able to detect, during a z-axis scan, the presence of the extra cellular matrix first, using through its wavelength dependence, and turn on data collection and image storing when the matrix is detected. While matrix detection and SHG are described, any desirable threshold level or frequency-dependent threshold may be used to control differential scanning.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed is:

1. A method for removing lipid from a biological sample, the method comprising:
   contacting a fixed biological sample with a composition in an amount and for a time sufficient to remove lipid, the composition comprising:
   sodium dodecyl sulfate (SDS), 3-(N,N-Dimethylmyristy-lammonio)propanesulfonate (SB3-14), polysorbate 20, t-octylphenoxypolyethoxyethanol, sodium deoxycholate, and a salt;
   wherein the contacting results in the sample being significantly free of lipid.

2. The method of claim 1, wherein the composition comprises about 1% to about 10% (weight:volume) of SDS.

3. The method of claim 1 wherein the composition comprises about 0.03% weight:volume (w/v) to about 3% w/v SB3-14.

4. The method of claim 1 wherein the composition comprises about 0.3% weight:volume (w/v) to about 3% w/v polysorbate 20.

5. The method of claim 1 wherein the composition comprises about 0.3% weight:volume (w/v) to about 3% w/v t-octylphenoxypolyethoxyethanol.

6. The method of claim 1 wherein the composition comprises about 0.1% weight:volume (w/v) to about 1% w/v sodium deoxycholate.

7. The method of claim 1 wherein the composition has a pH of from about 7 to about 9.

8. The method of claim 7 wherein the composition has a pH of from about 7.8 to about 8.8.

9. The method of claim 8 wherein the composition has a pH of from about 8.3 to about 8.5.

10. The method of claim 1, wherein the salt is selected from the group consisting of sodium chloride, calcium chloride and sodium metaborate.

11. The method of claim 10, wherein the salt is present in the composition at a concentration of from about 50 mM to about 500 mM.

12. The method of claim 11, wherein the salt is present in the composition at a concentration of 150 mM.

13. The method of claim 1, wherein the composition does not comprise boric acid.

14. The method of claim 1, wherein the composition does not comprise urea.

15. The method of claim 1, wherein the biological sample is fixed by embedding the biological sample in a fixative comprising acrylamide, paraformaldehyde, and optionally saponin.

16. The method of claim 1, wherein contacting comprises perfusing the biological sample with the composition.

17. The method of claim 16, wherein the biological sample is contacted with an antibody.

18. The method of claim 1, further comprising the step of contacting the biological sample with an imaging solution comprising 2,2'-thiodiethanol (TDE).

19. The method of claim 18 wherein the imaging solution comprises from about 1% to about 90% TDE.

20. The method of claim 1, wherein the biological sample is obtained from a plant or a eukaryote.

21. The method of claim 20 wherein the biological sample is obtained from a eukaryote.

22. The method of claim 21 wherein the biological sample is an organ, a tissue, or a cell taken from a multicellular organism.

23. The method of claim 21, wherein the eukaryote is a mouse embryo or a zebrafish.

24. The method of claim 22, wherein the organ is selected from the group consisting of heart, blood vessels, salivary gland, esophagus, stomach, liver, gallbladder, pancreas, intestine, colon, rectum, anus, endocrine gland, adrenal gland, kidney, ureter, bladder, lymph node, tonsils, adenoid, thymus, spleen, skin, muscle, brain, spinal cord, nerve, ovary, fallopian tube, uterus, vagina, mammary gland, testes, prostate, penis, pharynx, larynx, trachea, bronchi, lung, diaphragm, cartilage, ligaments, and tendon.

25. The method of claim 1, further comprising imaging the biological sample.

26. The method of claim 25, wherein the imaging is macroscale imaging.

27. The method of claim 25, wherein the imaging provides three-dimensional information.

28. The method of claim 26, wherein the macroscale imaging results in the ability to visualize the sample to a depth of about 5 µm, about 100 µm, about 200 µm, about 500 µm, about 1 mm, or about 10 mm.

* * * * *